US008771252B2

(12) United States Patent
Gelfand et al.

(10) Patent No.: US 8,771,252 B2
(45) Date of Patent: *Jul. 8, 2014

(54) METHODS AND DEVICES FOR RENAL NERVE BLOCKING

(75) Inventors: Mark Gelfand, New York, NY (US); Howard R. Levin, Teaneck, NJ (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 1404 days.

This patent is subject to a terminal disclaimer.

(21) Appl. No.: 11/133,925

(22) Filed: May 20, 2005

(65) Prior Publication Data

US 2006/0025821 A1 Feb. 2, 2006

Related U.S. Application Data

(63) Continuation of application No. 10/900,199, filed on Jul. 28, 2004, now Pat. No. 6,978,174, which is a continuation-in-part of application No. 10/408,665, filed on Apr. 8, 2003, now Pat. No. 7,162,303.

(60) Provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.
*A61M 31/00* (2006.01)

(52) U.S. Cl.
USPC .......................................................... 604/506

(58) Field of Classification Search
USPC ........ 607/3; 604/890.1, 891.1, 131, 151, 522, 604/506
See application file for complete search history.

(56) References Cited

U.S. PATENT DOCUMENTS

| 2,130,758 | A | 9/1938 | Rose |
| 2,276,995 | A | 3/1942 | Milinowski |
| 2,276,996 | A | 3/1942 | Milinowski |
| 3,043,310 | A | 7/1962 | Milinowski |
| 3,127,895 | A | 4/1964 | Kendall et al. |
| 3,181,535 | A | 5/1965 | Milinowski |
| 3,270,746 | A | 9/1966 | Kendall et al. |
| 3,329,149 | A | 7/1967 | Kendall et al. |
| 3,522,811 | A | 8/1970 | Schwartz et al |
| 3,563,246 | A | 2/1971 | Puharich et al. |
| 3,650,277 | A | 3/1972 | Sjostrand et al. |
| 3,670,737 | A | 6/1972 | Pearo |
| 3,752,162 | A | 8/1973 | Newash |
| 3,760,812 | A | 9/1973 | Timm et al. |

(Continued)

FOREIGN PATENT DOCUMENTS

| CA | 2575458 | 3/2006 |
| DE | 3151180 A1 | 8/1982 |

(Continued)

OTHER PUBLICATIONS

U.S. Appl. No. 11/504,117, Demarais et al.

(Continued)

*Primary Examiner* — Mark W Bockelman

(57) ABSTRACT

A method and apparatus for treatment of cardiac and renal diseases associated with the elevated sympathetic renal nerve activity by implanting a device to block the renal nerve signals to and from the kidney. The device can be a drug pump or a drug eluting implant for targeted delivery of a nerve-blocking agent to the periarterial space of the renal artery.

14 Claims, 9 Drawing Sheets

(56) References Cited

U.S. PATENT DOCUMENTS

| | | | |
|---|---|---|---|
| 3,774,620 | A | 11/1973 | Hansjurgens |
| 3,794,022 | A | 2/1974 | Nawracaj et al. |
| 3,800,802 | A | 4/1974 | Berry et al. |
| 3,803,463 | A | 4/1974 | Cover |
| 3,894,532 | A | 7/1975 | Morey |
| 3,895,639 | A | 7/1975 | Rodler |
| 3,897,789 | A | 8/1975 | Blanchard |
| 3,911,930 | A | 10/1975 | Hagfors et al. |
| 3,952,751 | A | 4/1976 | Yarger |
| 3,987,790 | A | 10/1976 | Eckenhoff et al. |
| 4,011,861 | A | 3/1977 | Enger |
| 4,026,300 | A | 5/1977 | DeLuca et al. |
| 4,055,190 | A | 10/1977 | Tany |
| 4,071,033 | A | 1/1978 | Nawracaj et al. |
| 4,105,017 | A | 8/1978 | Ryaby et al. |
| 4,141,365 | A | 2/1979 | Fischell et al. |
| 4,266,532 | A | 5/1981 | Ryaby et al. |
| 4,266,533 | A | 5/1981 | Ryaby et al. |
| 4,305,115 | A | 12/1981 | Armitage |
| 4,315,503 | A | 2/1982 | Ryaby et al. |
| 4,360,019 | A | 11/1982 | Portner et al. |
| 4,379,462 | A | 4/1983 | Borkan et al. |
| 4,405,305 | A | 9/1983 | Stephen et al. |
| 4,454,883 | A | 6/1984 | Fellus |
| 4,467,808 | A | 8/1984 | Brighton et al. |
| 4,487,603 | A | 12/1984 | Harris |
| 4,530,840 | A | 7/1985 | Tice et al. |
| 4,587,975 | A | 5/1986 | Salo et al. |
| 4,602,624 | A | 7/1986 | Naples et al. |
| 4,608,985 | A | 9/1986 | Crish et al. |
| 4,649,936 | A | 3/1987 | Ungar et al. |
| 4,671,286 | A | 6/1987 | Renault |
| 4,674,482 | A | 6/1987 | Waltonen et al. |
| 4,692,147 | A | 9/1987 | Duggan |
| 4,715,852 | A | 12/1987 | Reinicke et al. |
| 4,774,967 | A | 10/1988 | Zanakis |
| 4,791,931 | A | 12/1988 | Slate |
| 4,816,016 | A | 3/1989 | Schulte et al. |
| 4,852,573 | A | 8/1989 | Kennedy |
| 4,865,845 | A | 9/1989 | Eckenhoff et al. |
| 4,976,711 | A | 12/1990 | Parins et al. |
| 4,979,511 | A | 12/1990 | Terry, Jr. |
| 4,981,146 | A | 1/1991 | Bertolucci |
| 4,998,532 | A | 3/1991 | Griffith |
| 5,006,119 | A | 4/1991 | Acker et al. |
| 5,014,699 | A | 5/1991 | Pollack et al. |
| 5,019,034 | A | 5/1991 | Weaver et al. |
| 5,057,318 | A | 10/1991 | Magruder et al. |
| 5,058,584 | A | 10/1991 | Bourgeois |
| 5,059,423 | A | 10/1991 | Magruder et al. |
| 5,061,492 | A | 10/1991 | Okada et al. |
| 5,094,242 | A | 3/1992 | Gleason et al. |
| 5,111,815 | A | 5/1992 | Mower |
| 5,112,614 | A | 5/1992 | Magruder et al. |
| 5,125,928 | A | 6/1992 | Parins et al. |
| 5,131,409 | A | 7/1992 | Lobarev et al. |
| 5,137,727 | A | 8/1992 | Eckenhoff |
| 5,188,837 | A | 2/1993 | Domb |
| 5,193,048 | A | 3/1993 | Kaufman et al. |
| 5,193,539 | A | 3/1993 | Schulman et al. |
| 5,193,540 | A | 3/1993 | Schulman et al. |
| 5,199,428 | A | 4/1993 | Obel et al. |
| 5,203,326 | A | 4/1993 | Collins et al. |
| 5,213,098 | A | 5/1993 | Bennett et al. |
| 5,215,086 | A | 6/1993 | Terry, Jr. et al. |
| 5,231,988 | A | 8/1993 | Wernicke et al. |
| 5,234,692 | A | 8/1993 | Magruder et al. |
| 5,234,693 | A | 8/1993 | Magruder et al. |
| 5,251,634 | A | 10/1993 | Weinberg |
| 5,251,643 | A | 10/1993 | Osypka |
| 5,263,480 | A | 11/1993 | Wernicke et al. |
| 5,269,303 | A | 12/1993 | Wernicke et al. |
| 5,282,468 | A | 2/1994 | Klepinski |
| 5,282,785 | A | 2/1994 | Shapland et al. |
| 5,286,254 | A | 2/1994 | Shapland et al. |
| 5,299,569 | A | 4/1994 | Wernicke et al. |
| 5,300,068 | A | 4/1994 | Rosar et al. |
| 5,304,120 | A | 4/1994 | Crandell et al. |
| 5,304,206 | A | 4/1994 | Baker |
| 5,317,155 | A | 5/1994 | King |
| 5,324,255 | A | 6/1994 | Passafaro et al. |
| 5,324,316 | A | 6/1994 | Schulman et al. |
| 5,334,193 | A | 8/1994 | Nardella |
| 5,335,657 | A | 8/1994 | Terry, Jr. et al. |
| 5,338,662 | A | 8/1994 | Sadri |
| 5,351,394 | A | 10/1994 | Weinberg |
| 5,358,514 | A | 10/1994 | Schulman et al. |
| 5,368,591 | A | 11/1994 | Lennox et al. |
| 5,370,680 | A | 12/1994 | Proctor |
| 5,389,069 | A | 2/1995 | Weaver |
| 5,397,308 | A | 3/1995 | Ellis et al. |
| 5,397,338 | A | 3/1995 | Grey et al. |
| 5,400,784 | A | 3/1995 | Durand et al. |
| 5,405,367 | A | 4/1995 | Schulman et al. |
| 5,423,744 | A | 6/1995 | Gencheff et al. |
| 5,429,634 | A | 7/1995 | Narciso, Jr. |
| 5,433,739 | A | 7/1995 | Sluijter et al. |
| 5,439,440 | A | 8/1995 | Hofmann |
| 5,454,782 | A | 10/1995 | Perkins |
| 5,454,809 | A | 10/1995 | Janssen |
| 5,458,568 | A | 10/1995 | Racchini et al. |
| 5,458,626 | A | 10/1995 | Krause |
| 5,458,631 | A | 10/1995 | Xavier |
| 5,470,352 | A | 11/1995 | Rappaport |
| 5,472,406 | A | 12/1995 | de la Torre et al. |
| 5,478,303 | A | 12/1995 | Foley-Nolan et al. |
| 5,484,400 | A | 1/1996 | Edwards et al. |
| 5,494,822 | A | 2/1996 | Sadri |
| 5,498,238 | A | 3/1996 | Shapland et al. |
| 5,499,971 | A | 3/1996 | Shapland et al. |
| 5,505,700 | A | 4/1996 | Leone et al. |
| 5,507,724 | A | 4/1996 | Hofmann et al. |
| 5,507,791 | A | 4/1996 | Sit'ko |
| 5,531,778 | A | 7/1996 | Maschino et al. |
| 5,540,730 | A | 7/1996 | Terry, Jr. et al. |
| 5,540,734 | A | 7/1996 | Zabara |
| 5,553,611 | A | 9/1996 | Budd et al. |
| 5,560,360 | A | 10/1996 | Filler et al. |
| 5,569,198 | A | 10/1996 | Racchini |
| 5,571,147 | A | 11/1996 | Sluijter et al. |
| 5,571,150 | A | 11/1996 | Wernicke et al. |
| 5,573,552 | A | 11/1996 | Hansjurgens |
| 5,584,863 | A | 12/1996 | Rauch et al. |
| 5,589,192 | A | 12/1996 | Okabe et al. |
| 5,599,345 | A | 2/1997 | Edwards et al. |
| 5,618,563 | A | 4/1997 | Berde et al. |
| 5,626,576 | A | 5/1997 | Janssen |
| 5,626,862 | A | 5/1997 | Brem et al. |
| 5,628,730 | A | 5/1997 | Shapland et al. |
| 5,634,462 | A | 6/1997 | Tyler et al. |
| 5,634,899 | A | 6/1997 | Shapland et al. |
| 5,672,174 | A | 9/1997 | Gough et al. |
| 5,688,266 | A | 11/1997 | Edwards et al. |
| 5,689,877 | A | 11/1997 | Grill, Jr. et al. |
| 5,690,691 | A | 11/1997 | Chen et al. |
| 5,700,282 | A | 12/1997 | Zabara |
| 5,700,485 | A | 12/1997 | Berde et al. |
| 5,704,908 | A | 1/1998 | Hofmann et al. |
| 5,707,400 | A | 1/1998 | Terry, Jr. et al. |
| 5,711,326 | A | 1/1998 | Thies et al. |
| 5,713,847 | A | 2/1998 | Howard, III et al. |
| 5,722,401 | A | 3/1998 | Pietroski et al. |
| 5,723,001 | A | 3/1998 | Pilla et al. |
| 5,725,563 | A | 3/1998 | Klotz et al. |
| 5,728,396 | A | 3/1998 | Peery et al. |
| 5,747,060 | A | 5/1998 | Sackler et al. |
| 5,755,750 | A | 5/1998 | Petruska et al. |
| 5,756,115 | A | 5/1998 | Moo-Young et al. |
| 5,772,590 | A | 6/1998 | Webster, Jr. |
| 5,792,187 | A | 8/1998 | Adams |
| 5,800,464 | A | 9/1998 | Kieval |
| 5,807,306 | A | 9/1998 | Shapland et al. |
| 5,810,802 | A | 9/1998 | Panescu et al. |
| 5,814,079 | A | 9/1998 | Kieval |

(56) References Cited

U.S. PATENT DOCUMENTS

| | | |
|---|---|---|
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu |
| 5,893,885 A | 4/1999 | Webster et al. |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,922,340 A | 7/1999 | Berde et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,954,719 A | 9/1999 | Chen et al. |
| 5,983,131 A | 11/1999 | Weaver et al. |
| 5,983,141 A | 11/1999 | Sluijter et al. |
| 6,006,134 A | 12/1999 | Hill et al. |
| 6,009,877 A | 1/2000 | Edwards |
| 6,010,613 A | 1/2000 | Walters et al. |
| 6,026,326 A | 2/2000 | Bardy |
| 6,041,252 A | 3/2000 | Walker et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,117,101 A | 9/2000 | Diederich et al. |
| 6,122,548 A | 9/2000 | Starkebaum et al. |
| 6,123,718 A | 9/2000 | Tu et al. |
| 6,135,999 A | 10/2000 | Fanton et al. |
| 6,146,380 A | 11/2000 | Racz et al. |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,238,702 B1 | 5/2001 | Berde et al. |
| 6,245,026 B1 | 6/2001 | Campbell et al. |
| 6,246,912 B1 | 6/2001 | Sluijter |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,273,886 B1 | 8/2001 | Edwards et al. |
| 6,280,377 B1 | 8/2001 | Talpade |
| 6,283,951 B1 | 9/2001 | Flaherty et al. |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,488,679 B1 | 12/2002 | Swanson et al. |
| 6,506,189 B1 | 1/2003 | Rittman, III et al. |
| 6,508,774 B1 | 1/2003 | Acker et al. |
| 6,514,226 B1 | 2/2003 | Levin et al. |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,564,096 B2 | 5/2003 | Mest |
| 6,571,127 B1 | 5/2003 | Ben-Haim et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni et al. |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,635,054 B2 | 10/2003 | Fjield et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,738 B2 | 2/2004 | MacLaughlin et al. |
| 6,697,670 B2 | 2/2004 | Chomenky et al. |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,749,598 B1 | 6/2004 | Keren et al. |
| 6,767,544 B2 | 7/2004 | Brooks et al. |
| 6,786,904 B2 | 9/2004 | Doscher et al. |
| 6,795,728 B2 | 9/2004 | Chornenky et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,885,888 B2 | 4/2005 | Rezai |
| 6,893,414 B2 | 5/2005 | Goble et al. |
| 6,916,656 B2 | 7/2005 | Walters et al. |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,958,060 B2 | 10/2005 | Mathiesen et al. |
| 6,969,388 B2 | 11/2005 | Goldman et al. |

(56) References Cited

U.S. PATENT DOCUMENTS

| | | |
|---|---|---|
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,373,204 B2 | 5/2008 | Gelfand et al. |
| 7,444,183 B2 | 10/2008 | Knudson et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,717,948 B2 | 5/2010 | Demarais et al. |
| 7,756,583 B2 | 7/2010 | Demarais et al. |
| 7,917,208 B2 | 3/2011 | Yomtov et al. |
| 8,027,740 B2 | 9/2011 | Altman et al. |
| 8,131,371 B2 | 3/2012 | Demarais et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,465,752 B2 | 6/2013 | Seward |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050681 A1 | 3/2003 | Pianca et al. |
| 2003/0055422 A1 | 3/2003 | Lesh |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0082225 A1 | 5/2003 | Mason |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0192638 A1 | 9/2005 | Gelfand et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0095029 A1 | 5/2006 | Young et al. |
| 2006/0100667 A1 | 5/2006 | Machado et al. |

(56) References Cited

U.S. PATENT DOCUMENTS

| | | |
|---|---|---|
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem |
| 2007/0282376 A1 | 12/2007 | Shuros et al. |
| 2007/0288070 A1 | 12/2007 | Libbus et al. |
| 2008/0004596 A1 | 1/2008 | Yun et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0045890 A1 | 2/2008 | Seward et al. |
| 2008/0091255 A1 | 4/2008 | Caparso et al. |
| 2008/0140150 A1 | 6/2008 | Zhou et al. |
| 2008/0213331 A1 | 9/2008 | Gelfand et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2010/0010567 A1 | 1/2010 | Deem et al. |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2011/0104060 A1 | 5/2011 | Seward |
| 2011/0104061 A1 | 5/2011 | Seward |
| 2011/0112400 A1 | 5/2011 | Gelfand et al. |
| 2011/0137298 A1 | 6/2011 | Nguyen et al. |
| 2011/0178570 A1 | 7/2011 | Demarais et al. |
| 2011/0182912 A1 | 7/2011 | Evans et al. |
| 2011/0184337 A1 | 7/2011 | Evans et al. |
| 2011/0200171 A1 | 8/2011 | Beetel et al. |
| 2011/0202098 A1 | 8/2011 | Demarais et al. |
| 2011/0257564 A1 | 10/2011 | Demarais et al. |
| 2011/0264011 A1 | 10/2011 | Wu et al. |
| 2012/0172837 A1 | 7/2012 | Demarais et al. |
| 2012/0259269 A1 | 10/2012 | Meyer |
| 2012/0271277 A1 | 10/2012 | Fischell et al. |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0172815 A1 | 7/2013 | Perry et al. |
| 2013/0252932 A1 | 9/2013 | Seward |
| 2013/0274674 A1 | 10/2013 | Fischell et al. |
| 2013/0287698 A1 | 10/2013 | Seward |
| 2013/0296853 A1 | 11/2013 | Sugimoto et al. |

FOREIGN PATENT DOCUMENTS

| | | |
|---|---|---|
| EP | 0233100 | 8/1987 |
| EP | 0811395 A2 | 6/1997 |
| EP | 0774991 | 10/2003 |
| EP | 1598024 A2 | 11/2005 |
| EP | 2092957 A1 | 8/2009 |
| EP | 2352542 | 8/2011 |
| EP | 2429641 | 3/2012 |
| EP | 2528649 | 12/2012 |
| EP | 2656807 | 10/2013 |
| JP | 49009682 | 1/1974 |
| JP | 62181225 | 8/1987 |
| JP | 3041967 | 2/1991 |
| JP | 2004016333 | 1/2004 |
| JP | 2004503294 | 2/2004 |
| WO | WO-85/01213 | 3/1985 |
| WO | WO-91/04725 | 4/1991 |
| WO | WO-9220291 A1 | 11/1992 |
| WO | WO-93/02740 | 2/1993 |
| WO | WO-93/07803 | 4/1993 |
| WO | WO-94/00188 | 1/1994 |
| WO | WO-9411057 A1 | 5/1994 |
| WO | WO-96/04957 | 1/1995 |
| WO | WO-9525472 A1 | 9/1995 |
| WO | WO-95/33514 | 12/1995 |
| WO | WO-9600039 A1 | 1/1996 |
| WO | WO-96/11723 | 4/1996 |
| WO | WO-9641616 | 12/1996 |
| WO | WO-97/13550 | 4/1997 |
| WO | WO-9713463 A1 | 4/1997 |
| WO | WO-9736548 | 10/1997 |
| WO | WO-97/42990 | 11/1997 |
| WO | WO-97/49453 | 12/1997 |
| WO | WO-98/37926 | 9/1998 |
| WO | WO-98/43700 | 10/1998 |
| WO | WO-98/43701 | 10/1998 |
| WO | WO-9842403 A1 | 10/1998 |
| WO | WO-98/48888 | 11/1998 |
| WO | WO-99/33407 | 7/1999 |
| WO | WO-99/51286 | 10/1999 |
| WO | WO-99/52424 | 10/1999 |
| WO | WO-01/26729 | 4/2001 |
| WO | WO-0122897 | 4/2001 |
| WO | WO-0170114 | 9/2001 |
| WO | WO-0170114 A1 | 9/2001 |
| WO | WO-0195832 | 12/2001 |
| WO | WO-02/09808 | 2/2002 |
| WO | WO-02/26314 | 4/2002 |
| WO | WO-0226318 | 4/2002 |
| WO | WO-02/053207 | 7/2002 |
| WO | WO-02/070039 A2 | 9/2002 |
| WO | WO-02/070047 | 9/2002 |
| WO | WO-02/085448 | 10/2002 |
| WO | WO-02085192 A2 | 10/2002 |
| WO | WO-03/018108 | 3/2003 |
| WO | WO-03024311 | 3/2003 |
| WO | WO-03/028802 | 4/2003 |
| WO | WO-03/063692 | 8/2003 |
| WO | WO-03/071140 A2 | 8/2003 |
| WO | WO-03/076008 | 9/2003 |
| WO | WO-03/082080 | 10/2003 |
| WO | WO-03/082403 | 10/2003 |
| WO | WO-2004/026370 | 4/2004 |
| WO | WO-2004/026371 | 4/2004 |
| WO | WO-2004/026374 | 4/2004 |

(56) References Cited

FOREIGN PATENT DOCUMENTS

| WO | WO-2004/030718 | | 4/2004 |
|---|---|---|---|
| WO | WO-2004/032791 | | 4/2004 |
| WO | WO-2004/011055 | | 5/2004 |
| WO | WO-2004/028583 | | 8/2004 |
| WO | WO-2004/107965 | | 12/2004 |
| WO | WO-2005014100 | | 2/2005 |
| WO | WO-2005016165 | | 2/2005 |
| WO | WO-2005/032646 | A2 | 4/2005 |
| WO | WO-2005032646 | | 4/2005 |
| WO | WO-2005/041748 | A2 | 5/2005 |
| WO | WO-2005/065284 | | 7/2005 |
| WO | WO-2005/084389 | A2 | 9/2005 |
| WO | WO-2005/097256 | A2 | 10/2005 |
| WO | WO-2005110528 | | 11/2005 |
| WO | WO-2005110528 | A1 | 11/2005 |
| WO | WO-2005/123183 | | 12/2005 |
| WO | WO-2006/007048 | A2 | 1/2006 |
| WO | WO-2006018528 | A1 | 2/2006 |
| WO | WO-2006/031899 | A2 | 3/2006 |
| WO | WO-2006022790 | A1 | 3/2006 |
| WO | WO-2006041847 | | 4/2006 |
| WO | WO-2006041881 | | 4/2006 |
| WO | WO-2007008954 | | 1/2007 |
| WO | WO-2007035537 | | 3/2007 |
| WO | WO-2007078997 | A2 | 7/2007 |
| WO | WO-2007086965 | | 8/2007 |
| WO | WO-2007103879 | | 9/2007 |
| WO | WO-2007103881 | | 9/2007 |
| WO | WO-2007121309 | | 10/2007 |
| WO | WO-2007146834 | | 12/2007 |
| WO | WO-2008003058 | | 1/2008 |
| WO | WO-2008061150 | | 5/2008 |
| WO | WO-2008061152 | | 5/2008 |
| WO | WO-2008070413 | | 6/2008 |
| WO | WO-2010078175 | A1 | 7/2010 |
| WO | WO-2011094367 | | 8/2011 |
| WO | WO-2012161875 | | 11/2012 |
| WO | WO-2013028781 | | 2/2013 |
| WO | WO-2013059735 | | 4/2013 |
| WO | WO-2013063331 | | 5/2013 |
| WO | WO-2013112844 | | 8/2013 |
| WO | WO-2013169741 | | 11/2013 |

OTHER PUBLICATIONS

U.S. Appl. No. 11/599,649, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.
Bello-Reuss, E. et al., "Effects of Acute Unilateral Renal Denervation in the Rat," J Clin Invest, 1975;56:208-217.
U.S. Appl. No. 12/940,922, filed Nov. 5, 2010, Gelfand et al.
U.S. Appl. No. 12/790,639, filed May 28, 2010, Wu et al.
U.S. Appl. No. 12/871,457, filed Aug. 30, 2010, Wu et al.
U.S. Appl. No. 13/007,370, filed Jan. 18, 2011, Gelfand et al.
U.S. Appl. No. 12/996,897, filed Dec. 13, 2010, Demarais.
U.S. Appl. No. 13/009,748, filed Jan. 19, 2011, Beetel et al.
U.S. Appl. No. 12/910,631, filed Oct. 22, 2010, Wu et al.
International Search Report, PCT/US04/38498, Mailed Feb. 18, 2005, Applicant: G & L Consulting, LLC, 4 pages.
International Search Report and Written Opinion, PCT/US05/35693, Mailed on Mar. 8, 2006, Applicant: Ardian, Inc., 29 pages.
International Search Report and Written Opinion, PCT/US05/35757, Mailed on Dec. 27, 2006, Applicant: Ardian, Inc., 8 pages.
International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US06/48822, Mailed on Aug. 15, 2008, Applicant: Ardian, Inc., 12 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant: Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
International Search Report and Written Opinion for PCT/US2009/069334; Applicant: Ardian, Inc.; Mailing Date: Mar. 1, 2010, 10 pages.
European Search Report; European Patent Application No. 05806045.0; Applicant: Ardian, Inc.; Date of Mailing: Sep. 22, 2009, 8 pages.
European Search Report; European Patent Application No. 05811851.4; Applicant: Ardian, Inc.; Date of Mailing: Oct. 1, 2009, 7 pages.
European Search Report; European Patent Application No. 06847926.0; Applicant: Ardian, Inc.; Date of Mailing: Feb. 10, 2010, 6 pages.
European Search Report; European Patent Application No. 0775925.8; Applicant: Ardian, Inc.; Date of Mailing: Apr. 29, 2010, 9 pages.
European Search Report; European Patent Application No. 07799148.7; Applicant: Ardian, Inc.; Date of Mailing: Jul. 23, 2009, 6 pages.
European Search Report; European Patent Application No. 09156661.2; Applicant: Ardian, Inc.; Date of Mailing: Jul. 23, 2009, 6 pages.
European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
European Search Report; European Patent Application No. 07868755.5; Applicant: Ardian, Inc.; Date of Mailing: Jul. 28, 2010, 7 pages.
Bello-Reuss, E. et al., "Effect of renal sympathetic nerve stimulation on proximal water and sodium reabsorption," J Clin Invest, 1976;57:1104-1107.
Non-Final Office Action; U.S. Appl. No. 11/599,882; Mailed on Jul. 6, 2009, 13 pages.
Osborn, et al., "Effect of renal nerve stimulation on renal blood flow autoregulation and antinatriuresis during reductions in renal perfusion pressure," in Proceedings of the Society for Experimental Biology and Medicine, vol. 168, 77-81, 1981. (Abstract).
Solis-Herruzo, J.A. et al., "Effects of lumbar sympathetic block on kidney function in cirrhotic patients with hepatorenal syndrome," Journal of Hepatology, 1987; 5: 167-173.
Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.
Guimaraes, Sarfim. "Vascular Adrenoceptors: An Update" pp. 319-356.
Hammer, Leah W. "Differential Inhibition of Functional Dilation of Small Arterioles by Indomethacin and Glibenclamide." Hypertension. Feb. 2001 Part II. pp. 599-603.
Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.

(56) References Cited

OTHER PUBLICATIONS

Janda, J., "Impact of the electrical stimulation apparatus rebox on the course of ischemic renal damage in rats," British Library—"The world's knowledge" pp. 252-254 (translated and untranslated versions).

"2003 European Society of Hypertension-European Society of Cardiology guidelines for the management of arterial hypertension," Journal of Hypertension 2003, vol. 21, No. 6, pp. 1011-1053.

"Advances in the role of the sympathetic nervous system in cardiovascular medicine," 2001 SNS Report, No. 3, Springer, published with an educational grant from Servier, pp. 1-8.

"Electrical Stimulation for the Treatment of Chronic Wounds," Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pages.

"Electropermeabilization (Electroporation)," Cyto Pulse Sciences Inc., http://www.cytopulse.com/electroporation.html (last accessed Mar. 3, 2005), 3 pages.

"Electroporation based Technologies and Treatments," ESPE Newsletter No. 6, QLK 02002-2003, Jan. 2005, www.cliniporator.com, 4 pages.

"End-stage renal disease payment policies in traditional Medicare," Report to the Congress: Medicare Payment Policy, Mar. 2001, Medpac, pp. 123-138.

"Fact Book Fiscal Year 2003," National Institutes of Health National Heart, Lung, and Blood Institute, Feb. 2004, 197 pages.

"Heart Disease and Stroke Statistics-2004 update," American Heart Association, American Stroke Association, Dallas, Texas, ©2003 American Heart Association, 52 pages.

"Hypertension Incidence and Prevalence, Age Specific Rates, By Gender, B.C., 2001/2002," Graph., Chronic Disease Management, May 2003, British Columbia Ministry of Health Services, 1 page.

"Market for infusion pumps grows with an aging population," NWL 97-01, The BBI Newsletter, vol. 20, No. 2, Feb. 1, 1997, American Health Consultants Inc., 6 pages.

"PHCL 762 Pharmacology of the Autonomic Nervous System," Chapter 2 and 6.8 in Mosby, http://www.kumc.edu/research/medicine/pharmacology/CAI/phcl762.html, last accessed Aug. 24, 2004, 14 pages.

"Programmable Infusion System," Pumps and Pump Selection, Medtronic Pain Therapies, Medtronic, Inc. Sep. 5, 2001, 2 pages.

"Pulmonary Concepts in Critical Care Breath Sounds," http://rnbob.tripod.com/breath.htm, last accessed Aug. 23, 2004, 5 pages.

"Pulmonary Function Testing," http://jan.ucc.nau.edu/~daa/lecture/pft.htm, last accessed Aug. 23, 2004, 8 pages.

"Sensorcaine-MPF Spinal Injection," informational document, AstraZeneca 2001, 2 pages.

"Summary," Critical Reviews in Biomedical Engineering, vol. 17, Issue 5, 1989, pp. 515-529.

"The Antihypertensive and Lipid-Lowering Treatment to Prevent Heart Attack Trial," ALLHAT Research Group, JAMA 2002, vol. 288, pp. 2981-2997.

Aars, H. and S. Akre, "Reflex Changes in Sympathetic Activity and Arterial Blood Pressure Evoked by Afferent Stimulation of the Renal Nerve," Feb. 26, 1999, Acta Physiol. Scand., vol. 78, 1970, pp. 184-188.

Abramov, G.S. et al., "Alteration in sensory nerve function following electrical shock," Burns vol. 22, No. 8, ©1996 Elsevier Science Ltd., pp. 602-606.

Achar, Suraj, M.D. and Suriti Kundu, M.D., "Principles of Office Anesthesia: Part I. Infiltrative Anesthesia," Office Procedures, American Family Physician, Jul. 1, 2002, vol. 66, No. 1, pp. 91-94.

Agnew, William F. et al., "Evolution and Resolution of Stimulation-Induced Axonal Injury in Peripheral Nerve," May 21, 1999, Muscle and Nerve, vol. 22, Oct. 1999, ©1999 John Wiley & Sons, pp. 1393-1402.

Ahadian, Farshad M., M.D., "Pulsed Radiofrequency Neurotomy: Advances in Pain Medicine," Current Pain and Headache Reports 2004, vol. 8, ©2004 Current Science Inc., pp. 34-40.

Alford, J.Winslow, M.D. and Paul. D. Fadale, M.D., "Evaluation of Postoperative Bupivacaine Infusion for Pain Management After Anterior Cruciate Ligament Reconstruction," The Journal of Arthroscopic and Related Surgery October, vol. 19, No. 8, ©2003 Arthroscopy Association of North America, pp. 855-861.

Andrews, B.T. et al., "The use of surgical sympathectomy in the treatment of chronic renal pain," Mar. 5, 1997, British Journal of Urology, vol. 80, ©1997 British Journal of Urology, pp. 6-10.

Archer, Steffan et al., "Cell Reactions to Dielectrophoretic Manipulation," Mar. 1, 1999, Biochemical and Biophysical Research Communications, 1999 Academic Press, pp. 687-698.

Arias, Manuel J., M.D., "Percutaneous Radio Frequency Thermocoagulation with Low Temperature in the Treatment of Essential Glossopharyngeal Neuralgia," Surg. Neurol. 1986, vol. 25, ©1986 Elsevier Science Publishing Co. Inc., pp. 94-96.

Aronofsky, David H., D.D.S., "Reduction of dental postsurgical symptoms using nonthermal pulsed high-peak-power electromagnetic energy," Oral Surg., Nov. 1971, vol. 32, No. 5, pp. 688-696.

Aspelin, Peter, M.D., Ph.D. et al, "Nephrotoxic Effects in High-Risk Patients Undergoing Angiography," Feb. 6, 2003, New England Journal of Medicine 2003, vol. 348, No. 6, 2003 Massachusetts Medical Society, pp. 491-499.

Awwad, Ziad M., FRCS and Bashir A. Atiyat, GBA, JBA, "Pain relief using continuous bupivacaine infusion in the paravertebral space after loin incision," May 15, 2004, Saudi Med. J. 2004, vol. 25, No. 10, pp. 1369-1373.

Badyal, D.K., H. Lata and A.P. Dadhich, "Animal Models of Hypertension and Effect of Drugs," Aug. 19, 2003, Indian Journal of Pharmacology 2003, vol. 35, pp. 349-362.

Baker, Carol E. et al., "Effect of pH of Bupivacaine on Duration of Repeated Sciatic Nerve Blocks in the Albino Rat," Anesth. Analg, 1991, vol. 72, ©1991 The International Anesthesia Research Society, pp. 773-778.

Balazs, Tibor, "Development of Tissue Resistance to Toxic Effects of Chemicals," Jan. 26, 1974, Toxicology, vol. 2, ©1974 Elsevier/North Holland, Amsterdam, pp. 247-255.

Barrett, Carolyn J. et al., "Long-term control of renal blood flow: what is the role of renal nerves?" Jan. 4, 2001, Am. J. Physiol. Regulatory Integrative Comp. Physiol. 2001, vol. 280, © 2001 the American Physiological Society, pp. R1534-R1545.

Barrett, Carolyn J. et al., "What Sets The Long-Term Level of Renal Sympathetic Nerve Activity?," May 12, 2003, Integrative Physiology, Circulation Research 2003, vol. 92, ©2003 American Heart Association, pp. 1330-1336.

Bassett, C. Andrew L. et al., "Augmentation of Bone Repair by Inductively Coupled Electromanetic Fields," May 3, 1974, SCIENCE, vol. 184, pp. 575-577.

Bassett, C. Andrew L., "Fundamental and Practical Aspects of Therapeutic Uses of Pulsed Electromagnetic Fields (PEMFs)," Critical Reviews in Biomedical Engineering, vol. 17, No. 5, 1989, pp. 451-514.

Beebe, Stephen J. et al., "Nanosecond Pulsed Electric Field (nsPEF) Effects on Cells and Tissues: Apoptosis Induction and Tumor Growth Inhibition," Oct. 11, 2001, IEEE Transactions on Plasma Science, vol. 30, No. 1, Feb. 2002, © 2002 IEEE, pp. 286-292.

Beebe, Stephen J. et al., "Nanosecond pulsed electric fields modulate cell function through intracellular signal transduction mechanisms," Apr. 8, 2004, Physiological Measurement, vol. 25, 2004, ©2004 IOP Publishing Ltd., pp. 1077-1093.

Bhadra, Niloy and Kevin L. Kilgore, "Direct Current Electrical Conduction Block of Peripheral Nerve," Feb. 25, 2004, IEEE Transactions on Neural Systems and Rehabilitation Engineering, vol. 12, No. 3, Sep. 2004, pp. 313-324.

Bhatt, Deepak L. et al., "Rhabdomyolysis Due to Pulsed Electric Fields," May 11, 1989, Plastic and Reconstructive Surgery Jul. 1990, pp. 1-11.

Bigler, D. et al., "Tachyphylaxis during postoperative epidural analgesia-new insights," Apr. 15, 1987, Letter to the Editor, Acta Anesthesiol. Scand. 1987, vol. 31, pp. 664-665.

Binder, Allan et al., "Pulsed Electromagnetic Field Therapy of Persistent Rotator Cuff Tendinitis," The Lancet, Saturday Mar. 31, 1984, The Lancet Ltd., pp. 695-698.

(56) References Cited

OTHER PUBLICATIONS

Black, Henry R., M.D., "Resistant Hypertension 2004," presentation at Rush University Medical Center, Jul. 15, 2004, 40 pages.
Blair, M.L. et al., "Sympathetic activation cannot fully account for increased plasma renin levels during water deprivation," Sep. 23, 1996, Am J Physiol 1997, vol. 272, © 1997 the American Physiological Society, pp. R1197-R1203.
Blomberg, Sture G., M.D., Ph.D., "Long-Term Home Self-Treatment with High Thoracic Epidural Anesthesia in Patients with Severe Coronary Artery Disease," Mar. 29, 1994, Anesth. Analg. 1994, vol. 79, © 1994 International Anesthesia Research Society, pp. 413-421.
Cahana, Alex, M.D., "Pulsed Radiofrequency: A Neurobiologic and Clinical Reality," May 17, 2005, Anesthesiology 2005, vol. 103, No. 6, Dec. 2005, ©2005 American Society of Anesthesiologists, Inc., Lippincott Williams & Wilkins, Inc., p. 1311.
Calaresu, F.R. et al., "Haemodynamic Responses and Renin Release During Stimulation of Afferent Renal Nerves in the Cat," Aug. 12, 1975, J. Physiol. 1976, vol. 255, pp. 687-700.
Campese, V.M., "A new model of neurogenic hypertension caused by renal injury: pathophysiology and therapeutic implications," Clin. Exp. Nephrol 2003, vol. 7, ©2003 Japanese Society of Nephroloogy, pp. 167-171.
Campese, V.M., "Neurogenic factors and hypertension in chronic renal failure," Journal of Nephrology, vol. 10, No. 4, © 1997 Societa Italiana di Nefrologia, pp. 184-187.
Carls, G., et al., "Electrical and magnetic stimulation of the intercostal nerves: a comparative study," Electromyogr. clin. Neurophysiol., vol. 37, 1997, pp. 509-512.
Carlson, Scott H. and J. Michael Wyss, "e-Hyertension, Opening New Vistas," Introductory Commentary, Hypertension 2000, vol. 35, American Heart Association, Inc., 2000, p. 538.
Chang, Donald C., "Cell poration and cell fusion using an oscillating electric field," Biophysical Journal, vol. 56, Oct. 1989, Biophysical Society, pp. 641-652.
Chobanian, Aram V. et al., "Seventh Report of the Joint National Committee on Prevention, Detection, Evaluation, and Treatment of High Blood Pressure," Nov. 6, 2003, Hypertension 2003, vol. 42, © 2003 American Heart Association, Inc., pp. 1206-1252.
Conradi, E., Ines Helen Pages, "Effects of Continuous and Pulsed Microwave Irradiation on Distribution of Heat in the Gluteal Region of Minipigs," Scand. J. Rehab. Med., vol. 21, 1989, pp. 59-62.
Converse Jr., R.L. et al., "Sympathetic Overactivity in Patients with Chronic Renal Failure," New England Journal of Medicine, Dec. 31, 1992, vol. 327 (27), pp. 1912-1918.
Cosman, Eric R., Jr. et al., "Electric and Thermal Field Effects in Tissue Around Radiofrequency Electrodes," Pain Medicine, vol. 6, No. 6, 2005, American Academy of Pain Medicine, pp. 405-424.
Cosman, Eric R., Ph.D., "A Comment on the History of the Pulsed Radiofrequency Technique for Pain Therapy," Anesthesiology Dec. 2005, vol. 103, No. 6, ©2005 American Society of Anesthesiologists, Inc. Lippincott Williams & Wilkins, Inc., p. 1312.
Crawford, William H. et al., "Pulsed Radio Frequency Therapy of Experimentally Induced Arthritis in Ponies," Dec. 18, 1989, Can. J. Vet. Res. 1991, vol. 55, pp. 76-85.
Dahm, Peter et al., "Efficacy and Technical Complications of Long-Term Continuous Intraspinal Infusions of Opioid and/or Bupivacaine in Refractory Nonmalignant Pain . . . ," Oct. 6, 1997, The Clinical Journal of Pain 1998, vol. 14, No. 1, © 1998 Lippincott-Raven Publishers, pp. 4-16.
Dahm, Peter O. et al., "Long-Term Intrathecal Infusion of Opioid and/or Bupivacaine in the Prophylaxis and Treatment of Phantom Limb Pain," Neuromodulation 1998, vol. 1, No. 3, ©1998 International Neuromodulation Society, pp. 111-128.
Dang, Nicholas C. et al., "A Novel Approach to Increase Total Urine Output in Heart Failure: Renal Nerve Blockade," ACC 2005 poster, 1 page.
Davalos, R.V. et al., "Tissue Ablation with Irreversible Electroporation," Sep. 7, 2004, Annals of Biomedical Engineering, vol. 33, No. 2, © 2005 Biomedical Engineering Society, pp. 223-231.

De Leeuw, Peter W. et al., "Renal Vascular Tachyphylaxis to Angiotensin II: Specificity of the Response for Angiotensin," Dec. 28, 1981, Life Sciences, vol. 30, © 1982 Pergamon Press Ltd., pp. 813-819.
Deng, Jingdong et al., "The Effects of Intense Submicrosecond Electrical Pulses on Cells," Nov. 26, 2002, Biophysical Journal, vol. 84, Apr. 2003, ©2003 Biophysical Society, pp. 2709-2714.
Denton, Kate M. et al., "Differential Neural Control of Glomerular Ultrafiltration," Jan. 30, 2004, Proceedings of the Australian Physiological and Pharmacological Society Symposium: Hormonal, Metabolic and Neural Control of the Kidney, Clinical and Experimental Pharmacology and Physiology (2004), 31, pp. 380-386.
Dev, Nagendu B., Ph.D. et al., "Intravascular Electroporation Markedly Attenuates Neointima Formation After Balloon Injury of the Carotid Artery in the Rat," Journal of Interventional Cardiology, vol. 13, No. 5, 2000, pp. 331-338.
Dev, Nagendu B., Ph.D. et al., "Sustained Local Delivery of Heparin to the Rabbit Arterial Wall With an Electroporation Catheter," May 5, 1998, Catheterization and Cardiovascular Diagnosis 1998, vol. 45, © 1998 Wiley-Liss Inc., pp. 337-345.
Dibona, Gerald F. and Linda L. Sawin, "Role of renal nerves in sodium retention of cirrhosis and congestive heart failure," Sep. 27, 1990, Am J Physiol 1991, vol. 260, © 1991 the American Physiological Society, pp. R298-R305.
Dibona, Gerald F. and Ulla C. Kopp, "Neural Control of Renal Function," Physiological Reviews Jan. 1997, vol. 77, No. 1, © 1997 American Physiological Society, pp. 75-197.
Dibona, Gerald F., "Nervous Kidney—Interaction Between Renal Sympathetic Nerves and the Renin-Angiotensin System in the Control of Renal Function," Jun. 21, 2000, Hypertension 2000, vol. 36, 2000 American Heart Association, Inc., pp. 1083-1088.
Dibona, Gerald F., "Neural Control of the Kidney-Past, Present, and Future," Nov. 4, 2002, Novartis Lecture, Hypertension 2003, vol. 41, part 2, ©2002 American Heart Association, pp. 621-624.
Dibona, Gerald F., "Renal Innervation and Denervation: Lessons from Renal Transplantation Reconsidered," Artificial Organs, vol. 11, No. 6, Raven Press Ltd., © 1987 International Society for Artificial Organs, pp. 457-462.
Dibona, Gerald F., "The Sympathetic Nervous System and Hypertension," Dec. 4, 2003, Hypertension Highlights, Hypertension Feb. 2004, vol. 43, ©2004 American Heart Association, pp. 147-150.
Dibona, Gerald F., L.L. Sawin, "Effect of renal denervation on dynamic autoregulation of renal blood flow," Feb. 12, 2004, Am J Physiol Renal Physiol 286, pp. F1209-F1218.
Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, ©2001 American Heart Association, pp. 1153-1163.
Dorros, Gerald, M.D., "Renal Artery Stenting State of the Art," presentation, TCT, Washington D.C., Sep. 2003, 27 pages.
Dunn, Matthew D. et al., "Laparoscopic Nephrectomy in Patients With End-Stage Renal Disease and Autosomal Dominant Polycystic Kidney Disease," Oct. 25, 1999, American Journal of Kidney Diseases Apr. 2000, vol. 35, No. 4, © 2000 National Kidney Foundation, Inc., pp. 720-725.
Durand, D.M., "Electrical Field Effects in Hyperexcitable Neural Tissue: A Review," Radiation Protection Dosimetry, vol. 106, No. 4, 2003, Nuclear Technology Publishing, pp. 325-331.
Erdine, Serap and Alev Arat-Ozkan, "Resistant Hypertension," European Society of Hypertension Scientific Newsletter: Update on Hypertension Management, 2003, vol. 4, No. 15, 2 pages.
Fareed, Jawad, Ph.D. et al., "Some Objective Considerations for the Use of Heparins and Recombinant Hirudin in Percutaneous Transluminal Coronary Angioplasty," Seminars in Thrombosis and Hemostasis 1991, vol. 17, No. 4, © 1991 Thieme Medical Publishers, Inc., pp. 455-470.
Ferguson, D.R. et al., "Responses of the pig isolated renal artery to transmural electrical stimulation and drugs," Dec. 7, 1984, Br. J. Pharmac. 1985, vol. 84, © 1985 The Macmillan Press Ltd., pp. 879-882.

(56) References Cited

OTHER PUBLICATIONS

Fernandez-Ortiz, Antonio et al., "A New Approach for Local Intravascular Drug Delivery—Iontophoretic Balloon," Intravascular Iontophoretic Local Delivery, Circulation, vol. 89, No. 4, Apr. 1994, pp. 1518-1522.
Fields, Larry E. et al, "The Burden of Adult Hypertension in the United States 1999 to 2000—A Rising Tide," May 18, 2004, ©2004 the American Heart Association, Hypertension Oct. 2004, pp. 1-7.
Freeman, Scott A. et al., "Theory of Electroporation of Planar Bilayer Membranes: Predictions of the Aqueous Area, Change in Capacitance, and Pore-Pore Separation," Feb. 23, 1994, Biophysical Journal, Jul. 1994, vol. 67, © 1994 by the Biophysical Society, pp. 42-56.
Fukuoka, Yuko et al., "Imaging of neural conduction block by neuromagnetic recording," Oct. 16, 2002, Clinical Neurophysiology 2002, vol. 113, ©2002 Elsevier Science Ireland Ltd., pp. 1985-1992.
Gami, Apoor S., M.D. and Vesna D. Garovic, M.D., "Contrast Nephropathy After Coronary Angiography," Mayo Clin Proc. 2004, vol. 79, 2004 Mayo Foundation for Medical Education and Research, pp. 211-219.
Gaylor, D.C. et al., "Significance of Cell Size and Tissue Structure in Electrical Trauma," Jan. 26, 1998, J. Theor. Biol. 1988, vol. 133, © 1988 Academic Press Limited, pp. 223-237.
Ghoname, El-sayed A. et al., "Percutaneous electrical nerve stimulation: an alternative to TENS in the management of sciatica," Apr. 26, 1999, Pain 1999, vol. 83, © 1999 International Association for the Study of Pain / Published by Elsevier Science B.V., pp. 193-199.
Gimple, M.D., Lawrence et al., "Effect of Chronic Subcutaneous or Intramural Administration of Heparin on Femoral Artery Restenosis After Balloon Angioplasty in Hypercholesterolemic Rabbits" Laboratory Investigation, Circulation, vol. 86, No. 5, Nov. 1992, pp. 1536-1546.
Goldberger, Jeffrey J. et al., "New technique for vagal nerve stimulation," Jun. 2, 1999, Journal of Neuroscience Methods 91, ©1999 Elsevier Science B.V., pp. 109-114.
Gorbunov, F.E. et al., "The Use of Pulsed and Continuous Short Wave Diathermy (Electric Field) in Medical Rehabilitation of the Patients with Guillain-Barre Syndrome and Other Peripheral Myelinopathies," May 6, 1994, 5 pages (most of article in Russian language).
Greenwell, T.J. et al., "The outcome of renal denervation for managing loin pain haematuria syndrome," Oct. 30, 2003, Institute of Urology and Nephrology, London, UK, ©2004 BJU International, 4 pages.
Gruberg, Luis, M.D. et al., "The Prognostic Implications of Further Renal Function Deterioration Within 48 h of Interventional Coronary Procedures in Patients with Pre-existent Chronic Renal Insufficiency," Jun. 19, 2000, Journal of the American College of Cardiology 2000, vol. 36, No. 5, ©2000 by the American College of Cardiology, pp. 1542-1548.
Hajjar, Ihab, M.D., M.S. and Theodore A. Kotchen, M.D., "Trends in Prevalence, Awareness, Treatment, and Control of Hypertension in the United States, 1988-2000," JAMA, Jul. 9, 2003, vol. 290, No. 2, pp. 199-206.
Hamza, M.D., Mohamed A. et al., "Effect of the Duration of Electrical Stimulation on the Analgesic Response in Patients with Low Back Pain," Anesthesiology, vol. 91, No. 6, Dec. 1999, ©1999 American Society of Anesthesiologists, Inc., pp. 1622-1627.
Han, Hyo-Kyung and Gordon L. Amidon, "Targeted Prodrug Design to Optimize Drug Delivery," Mar. 21, 2000, AAPS Pharmsci. 2000, vol. 2, No. 1, article 6, pp. 1-11.
Higuchi, Yoshinori, M.D., Ph.D. et al., "Exposure of the Dorsal Root Ganglion in Rats to Pulsed Radiofrequency Currents Activates Dorsal Horn Lamina I and II Neurons," Dec. 4, 2001, Experimental Studies, Neurosurgery, vol. 50, No. 4, Apr. 2002, pp. 850-856.
Hildebrand, Keith R., D.V.M., Ph.D. et al., "Stability, Compatibility, and Safety of Intrathecal Bupivacaine Administered Chronically via an Implantable Delivery System," May 18, 2001, The Clinical Journal of Pain, vol. 17, No. 3, ©2001 Lippincott Williams & Wilkins Inc., pp. 239-244.

Hing, Esther, M.P.H. and Kimberly Middleton, B.S.N., M.P.H., "National Hospital Ambulatory Medical Care Survey: 2001 Outpatient Department Summary," Aug. 5, 2003, Advance Data From Vital and Health Statistics, No. 338, CDC, 32 pages.
Horwich, Tamara, M.D., "New Advances in the Diagnosis and Management of Acute Decompensated Heart Failure," the Heart.org Satellite program, Rapid Review, CME Symposium presented on Nov. 8, 2004 at the Sheraton New Orleans Hotel, 4 pages.
Huang, Yifei et al., "Remodeling of the chronic severely failing ischemic sheep heart after coronary microembolization: functional, energetic, structural, and cellular responses," Jan. 8, 2004, Am J Physiol. 2004, vol. 286, ©2004 the American Physiological Society, pp. H2141-H2150.
Hughes, Gordon B., M.D. et al., "A Comparative Study of Neuropathologic Changes Following Pulsed and Direct Current Stimulation of the Mouse Sciatic Nerve," Jun. 27, 1980, American Journal of Otolaryngology, Nov. 1980, vol. 1, No. 5, pp. 378-384.
Israili, Z.H., "Clinical pharmacokinetics of angiotensin II (AT) receptor blockers in hypertension," Journal of Human Hypertension 2000, Macmillan Publishers Ltd., vol. 14, pp. S73-S86.
Janssen, Ben J.A. et al., "Effects of complete renal denervation and selective afferent renal denervation on the hypertension induced by intrarenal norepinephrine infusion on conscious rats," Jan. 4, 1989, Journal of Hypertension 1989, vol. 7, No. 6, © 1989 Current Science Ltd., pp. 447-455.
Johansson, Bjorn, "Electrical Membrane Breakdown, A Possible Mediator of the Actions of Electroconvulsive Therapy," Medical Hypotheses 1987, vol. 24, © 1987 Longman Group UK Ltd., pp. 313-324.
Jorgensen, William A. et al., "Electrochemical Therapy of Pelvic Pain: Effects of Pulsed Electromagnetic Fields (PEMF) on Tissue Trauma," Eur. J. Surg. 1994, vol. 160, Suppl. 574, © 1994 Scandinavian University Press, pp. 83-86.
Joshi, R.P. et al., "Improved energy model for membrane electroporation in biological cells subjected to electrical pulses," Apr. 9, 2002, Physical Review E, vol. 65, 041920-1, ©2002 The American Physical Society, 8 pages.
Joshi, R.P. et al., "Self-consistent simulations of electroporation dynamics in biological cells subjected to ultrashort electrical pulses," Jun. 21, 2001, Physical Review E, vol. 64, 011913, ©2001The American Physical Society, pp. 1-10.
Joshi, R.P., K.H. Schoenbach, "Mechanism for membrane electroporation irreversibility under high-intensity, ultrashort electrical pulse conditions," Nov. 11, 2002, Physical Review 2002, E 66, ©2002 The American Physical Society, pp. 052901-1-052901-4.
Kanduser, Masa et al., "Effect of surfactant polyoxyethylene glycol ($C_{12}$ $E_8$) on electroporation of cell line DC3F," Aug. 20, 2002, Colloids and Surfaces A: Physiochem. Eng. Aspects 2003, vol. 214, ©2002 Elsevier Science B.V., pp. 205-217.
Katholi, Richard E., "Renal nerves in the pathogenesis of hypertension in experimental animals and humans," Am J Physiol., vol. 245, © 1983 the American Physiological Society, pp. F1-F14.
Kelleher, Catherine L. et al., "Characteristics of Hypertension in Young Adults With Autosomal Dominant Polycystic Kidney Disease Compared With the General U.S. Population," Jun. 9, 2004, American Journal of Hypertension 2004, pp. 1029-1034.
King, Ronald W.P., "Nerves in a Human Body Exposed to Low-Frequency Electromagnetic Fields," Jun. 7, 1999, IEEE Transactions on Biomedical Engineering Dec. 1999, vol. 46, No. 12, © 1999 IEEE, pp. 1426-1431.
Kinney, Brian M., M.D., "High-Tech Healing—The evolution of therapeutic electromagnetic fields in plastic surgery," Plastic Surgery Products, Jun. 2004, pp. 32-36, 3 pages.
Kok, R.J. et al., "Specific Delivery of Captopril to the Kidney with the Prodrug Captopril-Lysozyme," Aug. 16, 1998, The Journal of Pharmacology and Experimental Therapeutics, vol. 288, No. 1, © 1999 by the American Society for Pharmacology and Experimental Therapeutics, pp. 281-285.
Kon, Valentina, "Neural Control of Renal Circulation," Miner Electrolyte Metab 1989, vol. 15, © 1989 S. Karger AG, pp. 33-43.
Koyama, Shozo et al., "Relative Contribution of Renal Nerve and Adrenal Gland to Renal Vascular Tone During Prolonged Canine Hemorrhagic Hypotension," Sep. 24, 1992, Circulatory Shock 1993, vol. 39, © 1993 Wiley-Liss Inc., pp. 269-274.

(56) References Cited

OTHER PUBLICATIONS

Kozak, Lola Jean, Ph.D. et al., "National Hospital Discharge Survey: 2001 Annual Summary with Detailed Diagnosis and Procedure Data," Vital Health Statistics, Series 13, No. 156, Jun. 2004, CDC, 206 pages.

Lafayette, Richard A., M.D., "How Does Knocking Out Angiotensin II Activity Reduce Renal Injury in Mice?" Jun. 14, 1999, Journal Club, American Journal of Kidney Diseases, vol. 35, No. 1, Jan. 2000, ©2000 National Kidney Foundation Inc., pp. 166-172.

Lavie, Peretz, Ph.D. and Victor Hoffstein, M.D., "Sleep Apnea Syndrome: A Possible Contributing Factor to Resistant Hypertension," Jun. 2001, Sleep 2001, vol. 24, No. 6, pp. 721-725.

Lee, Raphael C. and Jurgen Hannig, "Membrane Biology and Biophysics," Chapter 25, Surgical Research, © 2001 Academic Press, pp. 297-305.

Lee, Raphael C., M.D., Sc.D. and Michael S. Kolodney, S.B., "Electrical Injury Mechanisms: Electrical Breakdown of Cell Membranes," Oct. 1, 1986, Plastic and Reconstructive Surgery Nov. 1987, vol. 80, No. 5, pp. 672-679.

Ligtenberg, Gerry, M.D. et al., "Reduction of Sympathetic Hyperactivity by Enalapril in Patients with Chronic Renal Failure," Apr. 29, 1999, New England Journal of Medicine 1999, vol. 340, No. 17, ©1999 Massachusetts Medical Society, pp. 1321-1328.

Lin, Vernon W. H. et al, "High intensity magnetic stimulation over the lumbosacral spine evokes antinociception in rats," Apr. 16, 2002, Clinical Neurophysiology, vol. 113, © 2002 Elsevier Science Ireland Ltd., pp. 1006-1012.

Lipfert, Peter, M.D. et al., "Tachyphylaxis to Local Anesthetics Does Not Result From Reduced Drug Effectiveness at the Nerve Itself," Aug. 3, 1988, Anesthesiology 1989, vol. 70, pp. 71-75.

Lohmeier Thomas E. et al, "Baroreflexes prevent neurally induced sodium retention in angiotensin hypertension," Am. J. Physiol. Regulatory Integrative Comp. Physiol., vol. 279, © 2000 the American Physiological Society, pp. R1437-R1448.

Lohmeier, Thomas E. and Drew A. Hildebrandt, "Renal Nerves Promote Sodium Excretion in Angiotensin-Induced Hypertension," Oct. 20, 1997, Hypertension 1998, vol. 31, Part 2, © 1998 American Heart Association, Inc., pp. 429-434.

Lohmeier, Thomas E. et al., "Prolonged Activation of the Baroflex Produces Sustained Hypotension," Harry Goldblatt Award, Nov. 26, 2003, Hypertension 2004, vol. 43, part 2, ©2004 American Heart Association, Inc., pp. 306-311.

Lohmeier, Thomas E. et al., "Renal Nerves Promote Sodium Excretion During Long-Term Increases in Salt Intake," Oct. 23, 1998, Hypertension 1999, vol. 33, part 2, © 1999 American Heart Association, pp. 487-492.

Lohmeier, Thomas E. et al., "Sustained influence of the renal nerves to attenuate sodium retention in angiotensin hypertension," Apr. 13, 2001, Am J Physiol Regulatory Integrative Comp. Physiol., vol. 281, ©2001 the American Physiological Society, pp. R434-R443.

Lohmeier, Thomas E., "Interactions Between Angiotensin II and Baroreflexes in Long-Term Regulation of Renal Sympathetic Nerve Activity," Circulation Research, Jun. 27, 2003, ©2003 American Heart Association Inc., pp. 1282-1284.

Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.

Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.

Maeder, Micha, M.D. et al., "Contrast Nephropathy: Review Focusing on Prevention," Jun. 22, 2004, Journal of the American College of Cardiology Nov. 2, 2004, vol. 44, No. 9, ©2004 by the American College of Cardiology Foundation, pp. 1763-1771.

Malpas, Simon C., "What sets the long-term level of sympathetic nerve activity: is there a role for arterial baroreceptors?" Invited Review, Am J Physiol Regul. Integr. Comp. Physiol. 2004, vol. 286, ©2004 the American Physiological Society, pp. R1-R12.

Marenzi, Giancarlo, M.D. et al., "The Prevention of Radiocontrast-Agent-Induced Nephropathy by Hemofiltration," New England Journal of Medicine, Oct. 2, 2003, vol. 349 (14), ©2003 Massachusetts Medical Society, pp. 1333-1340.

U.S. Appl. No. 60/236,420, Harrison et al.

"Atrial Fibrillation" Heart and Vascular Health on Yahoo! Health. 2 pages. <URL: http://health.yahoo.com/topic/heart/overview/article/healthwise/hw160872;_ylt=AiBT43Ey74HQ7ft3jAb4C.sPu7cF>.

"Heart Arrhythmia" Heart and Vascular Health on Yahoo! Health. 13 pages. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF>.

"Isovue: Data Sheet". Regional Health Limited. 8 pages. Mar. 11, 2003.

"Micro ETS Hyperhidrosis USA" Hyperhidrosis USA. 2 pages. <URL: http://www.hyperhidrosis-usa.com/Index.html>.

Amersham Health. "Hypaque-Cysto" 6 pages. 2003.

Arentz, Thomas et al. "Incidence of pulmonary vein stenosis 2 years after radiofrequency catheter ablation of refractory atrial fibrillation." European Heart Journal. 2003. 24; pp. 963-969.

Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.

Bourge, Robert C. "Heart Failure Monitoring Devices: Rationale and Status" 28 pages.

Burkhoff, Daniel. "Interventional Device-Based Therapy for CHF Will Redefine Current Treatment Paradigms". Columbia University. 2004. 32 slides.

Canbaz, Suat et al. "Electrophysiological evaluation of phrenic nerve injury during cardiac surgery—a prospective, controlled clinical study." BioMed Central. 5 pages. 2004.

Carson, Peter. "Device-based Treatment for Chronic Heart Failure: Electrical Modulation of Myocardial Contractility". Transcatheter Cardiovascular Therapeutics 2005. 21 slides.

Chiou, CW et al. "Efferent Vagal Innervation of the Canine Atria and Sinus and Atrioventricular Nodes". Circulation. Jun. 1997. 95(11):2573-2584. Abstract only. 2 pages.

Cryovascular Systems, Inc. "Pre-Clinical Testing Establishing Parameters". PowerPoint Presentation. 18 slides.

Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.

Dong, Jun et al. "Incidence and Predictors of Pulmonary Vein Stenosis Following Catheter Ablation of Atrial Fibrillation Using the Anatomic Pulmonary Vein Ablation Approach: Results from Paired Magnetic Resonance Imaging." Journal of Cardiovascular Electrophysiology. vol. 16, No. 8, Aug. 2005. pp. 845-852.

Fava, M. "Clinical Testing Establishing Safety & Efficacy". PowerPoint Presentation. Cryovascular Systems, Inc. 14 slides.

Fava, M. et al. "Initial Human Experience with CryoPlasty™ in the Treatment of Infrainguinal Arterial Disease." Abstract. 1 page.

Fischell, Tim A. et al. "Ultrasonic Energy: Effects on Vascular Function and Integrity." Circulation: Journal of the American Heart Association. 1991. 84;pp. 1783-1795.

Hodgkin, Douglas D. et al. "Electrophysiologic Characteristics of a Pulsed Iontophoretic Drug-Delivery System in Coronary Arteries." Journal of Cardiovascular Pharmacology. 29(1):pp. 39-44, Jan. 1997. Abstract. 2 pages.

Jia, Jianping and Pollock, Martin. "The pathogenesis of non-freezing cold nerve injury: Observations in the rat." Brain. 120; pp. 631-646. 1997.

Jia, Jianping et al. "Cold injury to nerves is not due to ischaemia alone." Brain. 121;pp. 989-1001. 1998.

Jin, Yuanzhe. et al. "Pulmonary Vein Stenosis and Remodeling After Electrical Isolation for Treatment of Atrial Fibrillation: Short- and Medium-Term Follow-Up." PACE, vol. 27. pp. 1362-1370. Oct. 2004.

Joye, James D. and Tatsutani, Kristine. "In Vitro Studies of Arterial Freezing Injury". 4 pages.

(56) References Cited

OTHER PUBLICATIONS

Joye, James D. and Tatsutani, Kristine. "In Vivo Study of Endovascular Cryotherapy for the Prevention of Restenosis." 4 pages.
Knot, Harm J. and Nelson, Mark T. "Regulation of arterial diameter and wall [Ca2+] in cerebral arteries of rat by membrane potential and intravascular pressure." The Journal of Physiology. 1998. 508; pp. 199-209.
Kok, Lai Chow et al. "Effect of Heating on Pulmonary Veins: How to Avoid Pulmonary Vein Stenosis." Journal of Cardiovascular Electrophysiology. vol. 14, No. 3, Mar. 2003. pp. 250-254.
Mathur, Vandana S. "Intra-Renal Drug Delivery for Fluid Overload". FlowMedica. Transcatheter Cardiovascular Therapeutics 2005. 31 slides.
Mehran, Roxana. "Renal insufficiency and contrast nephropathy: The most common, least understood risk factor". Cardiovascular Research Foundation. Columbia University Medical Center. 2005. 86 slides.
Packer, Douglas L. et al. "Clinical Presentation, Investigation, and Management of Pulmonary Vein Stenosis Complicating Ablation for Atrial Fibrillation." Circulation: Journal of the American Heart Association. Feb. 8, 2005. pp. 546-554.
Pappone, Carlo and Santinelli, Vincenzo. "[2005][P2-70] Safety Report of Circumferential Pulmonary Vein Ablation. A 9-Year Single-Center Experience on 6,442 Patients with Atrial Fibrillation." Abstract only. 1 page.
Pappone, Carlo et al. "[2004][759] Pulmonary Vein Denervation Benefits Paroxysmal Atrial Fibrillation Patients after Circumferential Ablation." Abstract only. 1 page.
Purerfellner, Helmut and Martinek, Martin. "Pulmonary vein stenosis following catheter ablation of atrial fibrillation." Current Opinion in Cardiology. 20; pp. 484-490. 2005.
Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2, Feb. 2003. pp. 158-164.
Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.
Sabbah, Hani N. "Animal Models for Heart Failure and Device Development". Henry Ford Health System. 24 slides.
Schauerte, P. et al. "Catheter ablation of cardiac autonomic nerves for prevention of vagal atrial fibrillation." Circulation. 102(22). Nov. 28, 2000. Abstract only. 2 pages.
Schauerte, P. et al. "Focal atrial fibrillation: experimental evidence for a pathophysiologic role of the autonomic nervous system." Journal of Cardiovascular Electrophysiology. 12(5). May 2001. Abstract only. 2 pages.
Schauerte, P. et al. "Transvenous parasympathetic nerve stimulation in the inferior vena cava and atrioventricular conduction." Journal of Cardiovascular Electrophysiology. 11(1). Jan. 2000. Abstract only. 2 pages.
Scherlag, BJ and Po, S. "The intrinsic cardiac nervous system and atrial fibrillation." Current Opinion in Cardiology. 21(1):51-54, Jan. 2006. Abstract only. 2 pages.
Schmitt, Joseph et al. "Intravascular Optical Coherence Tomography—Opening a Window into Coronary Artery Disease". LightLab Imaging, Inc. Business Briefing: European Cardiology 2005.
Serrador, Jorge M. "Autonomic Regulation of the Cardiovascular System". MIT Lecture. 8 pages, 48 slides.
Siegel, RJ et al. "Clinical demonstration that catheter-delivered ultrasound energy reverses arterial vasoconstriction." Journal of the American College of Cardiology. 1992. 20; 732-735. Summary only. 2 pages.
Sobotka, Paul A. "Treatment Strategies for Fluid Overload, CHF Patients". CHF Solutions Transcatheter Cardiovascular Therapeutics 2005. 20 slides.
Steffen, W. et al. "Catheter-delivered high intensity, low frequency ultrasound induces vasodilation in vivo." European Heart Journal. 1994. 15;pp. 369-376.
Steg, PG et al. "Pulsed ultraviolet laser irradiation produces endothelium-independent relaxation of vascular smooth muscle". Circulation: Journal of the American Heart Association. 1989. pp. 189-197.
Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats". Pathophysiology of Haemostasis and Thrombosis. Dec. 23, 2002. pp. 184-189.
Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation." Journal of Intervocational Cardiac Electrophysiology. 14; pp. 41-25. 2005.
Terashima, Mitsuyasu et al. "Feasibility and Safety of a Novel CryoPlasty™ System". Poster. 1 page.
Thomas, John R. and Oakley, E. Howard N. "Chapter 15: Nonfreezing Cold Injury" Medical Aspects of Harsh Environments, vol. 1. pp. 467-490.
Vince, D. Geoffrey. "Virtual Histology: A new technique for the assessment of plaque composition". The Cleveland Clinic Foundation. 28 pages.
Yu, Wen-Chung et al. "Acquired Pulmonary Vein Stenosis after Radiofrequency Catheter Ablation of Paroxysmal Atrial Fibrillation." Journal of Cardiovascular Electrophysiology. vol. 12, No. 8. Aug. 2001. pp. 887-892.
Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.
McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.
McCullough, Peter A., M.D., MPH et al., "Acute Renal Failure after Coronary Intervention: Incidence, Risk Factors and Relationship to Mortality," Apr. 14, 1997, Am J Med. 1997, vol. 103, 1997 Excerpta Medica, Inc., pp. 368-375.
McMurray, John J.V., M.D. and Eileen O'Meara, M.D., "Treatment of Heart Failure with Spironolactone-Trial and Tribulations," Aug. 5, 2004, New England Journal of Medicine, vol. 351, No. 6, ©2004 Massachusetts Medical Society, pp. 526-528.
McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.
Medtronic Neurostimulation Systems, "Expanding the Array of Pain Control Solutions," informational pamphlet, 1999 Medtronic, Inc., 6 pages.
Medtronic, "Spinal Cord Stimulation," Patient Management Guidelines for Clinicians, Medtronic; Inc. 1999, 115 pages.
Medtronic, "SynchroMed Infusion System—Clinical Reference Guide for Pain Therapy," Medtronic, Inc. 1998, 198 pages.
Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, ©2003 Lippincott Williams & Wilkins, pp. 465-467.
Mihran, Richard T. et al., "Temporally-Specific Modification of Myelinated Axon Excitability in Vitro Following a Single Ultrasound Pulse," Sep. 25, 1989, Ultrasound in Med.& Biol. 1990, vol. 16, No. 3, pp. 297-309.
Mitchell, G.A.G., "The Nerve Supply of the Kidneys," Aug. 20, 1949, Acta Anatomica, vol. 10, Fasc. 1/2, 1950, pp. 1-37.
Moss, Nicholas G., "Renal function and renal afferent and efferent nerve activity," Am J Physiol 1982, vol. 243, © 1982, the American Physiological Society, pp. F425-F433.
Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.
Naropin (ropivacaine HCl) injection, Rx only description, AstraZeneca 2001, 3 pages.

(56) References Cited

OTHER PUBLICATIONS

National High Blood Pressure Education Program, "1995 Update of the Working Group Reports on Chronic Renal Failure and Renovascular Hypertension," presentation, 13 pages.
National Kidney Foundation, "Are You At Increased Risk for Chronic Kidney Disease?" ©2002 National Kidney Foundation, Inc., 14 pages.
Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, ©2003 MedReviews, LLC, pp. S7-S14.
Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, ©2004 Massachusetts Medical Society, pp. 585-592.
Peacock, J.M. and R. Orchardson, "Action potential conduction block of nerves in vitro by potassium citrate, potassium tartrate and potassium oxalate," May 6, 1998, Journal of Clinical Periodontology, ©1999 Munksgaard, vol. 26, pp. 33-37.
Pettersson, A. et al., "Renal interaction between sympathetic activity and ANP in rats with chronic ischaemic heart failure," Nov. 25, 1998, Acta Physiol. Scand. 1989, vol. 135, pp. 487-492.
Pliquett, U., "Joule heating during solid tissue electroporation," Oct. 22, 2002, Medical & Biological Engineering and CompUting 2003, vol. 41, pp. 215-219.
Popovic, Jennifer .R. and Margaret J. Hall,"1999 National Hospital Discharge Survey," Advance Data, No. 319, CDC, pp. 1-17 & 20.
Practice Guidelines Writing Committee and ESH/ESC Hypertension Guidelines Committee, "Practice Guidelines for Primary Care Physicians: 2003 ESH/ESC Hypertension Guidelines," Published in Journal of Hypertension 2003, vol. 21, No. 10: 1011-1053, ©2003 European Society of Hypertension, pp. 1779-1786.
Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.
Raji, A. R. M. and R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.
Ram, C. Venkata S., M.D., "Understanding refractory hypertension," May 15, 2004, Patient Care May 2004, vol. 38, pp. 12-16, 7 pages from http://www.patientcareonline.com/patcare/content/printContentPopup.jsp?id=108324.
Ravalia, A. et al., "Tachyphylaxis and epidural anesthesia," Edgware General Hospital, Correspondence, p. 529, 1989.
Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.
Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, ©2004 American Society of Anesthesiologists, Inc. Lippincott Williams & Wilkins, Inc., pp. 1-3.
Rihal, Charanjit S. et al., "Incidence and Prognostic Importance of Acute Renal Failure After Percutaneous Coronary Intervention," Mar. 6, 2002, Circulation May 14, 2002, vol. 10, ©2002 American Heart Association, Inc., pp. 2259-2264.
Rosen, S.M. et al., "Relationship of Vascular Reactivity to Plasma Renin Concentration in Patients with Terminal Renal Failure," Proc. Dialysis Transplant Forum 1974, pp. 45-47.
Roth, Bradley J. and Peter J. Basser, "A Model of the Stimulation of a Nerve Fiber by Electromagnetic Induction," IEEE Transactions on Biomedical Engineering, vol. 37, No. 6, Jun. 1990, pp. 588-597.
Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.
Rudnick, Michael R. et al., "Contrast-induced nephropathy: How it develops, how to prevent it," Cleveland Clinic Journal of Medicine Jan. 2006, vol. 73, No. 1, pp. 75-87.
Ruohonen, Jarmo et al., "Modeling Peripheral Nerve Stimulation Using Magnetic Fields," Journal of the Peripheral Nervous System 1997, vol. 2, No. 1, © 1997 Woodland Publications,. pp. 17-29.
Scheiner, Avram, Ph.D., "The design, development and implementation of electrodes used for functional electrical stimulation," Thesis paper, Case Western Reserve University, May 1992, 220 pages.
Schoenbach, Karl H. et al., "Intracellular Effect of Ultrashort Electrical Pulses," Dec. 26, 2000, Bioelectromagnetics 2001, vol. 22, ©2001 Wiley-Liss Inc., pp. 440-448.
Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, ©2002 American Society of Nephrology, pp. 1733-1739.
Scremin, Oscar U., M.D., Ph.D. and Danel P. Holschneider, M.D., "31. & 32. An Implantable Bolus Infusion Pump for the Neurosciences," FRP, 04-05, 3 pages.
Shu-Qing, Liu et al., "Old spinal cord injury treated by pulsed electric stimulation," General Hospital of Beijing Command, Beijing, 5 pages (full article in Chinese; abstract on last page), 1990.
Shupak, Naomi M., "Therapeutic Uses of Pulsed Magnetic-Field Exposure: A Review," Radio Science Bulletin Dec. 2003, No. 307, pp. 9-32.
Simpson, B. et al, "Implantable Spinal Infusion Devices for Chronic Pain and Spasticity: An Accelerated Systematic Review," ASERNIP-S Report No. 42, May 2003, 56 pages.
Sisken, B.F. et al., "229.17 Influence of Non-Thermal Pulsed Radiofrequency Fields (PRF) on Neurite Outgrowth," Society for Neuroscience, vol. 21, 1995, 2 pages.
Skeie, B. et al., "Effect of chronic bupivacaine infusion on seizure threshold to bupivacaine," Dec. 28, 1986, Acta Anaesthesiol. Scand. 1987, vol. 31, pp. 423-425.
Skopec, M., "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006.
Slappendel, Robert et al., "The efficacy of radiofrequency lesioning of the cervical spinal dorsal root ganglion in a double blinded randomized study," Jun. 26, 1997, Pain, vol. 73, © 1997 International Association of the Study of Pain, Elsevier Science B.V., pp. 159-163.
Sluijter, M.D., Ph.D., "Pulsed Radiofrequency," May 17, 2005, Anesthesiology Dec. 2005, vol. 103, No. 6, ©2005 American Society of Anesthesiologists, Inc. Lippincott Williams & Wilkins, Inc., pp. 1313-1314.
Sluijter, M.D., Ph.D., "Radiofrequency Part 1: The Lumbosacral Region," Chapter 1 Mechanisms of Chronic Pain and part of Chapter 2 Spinal Pain, ©2001 FlivoPress SA, Meggen (LU), Switzerland, pp. 1-26.
Sluijter, M.D., Ph.D., "The Role of Radiofrequency in Failed Back Surgery Patients," Current Review of Pain 2000, vol. 4, ©2000 by Current Science Inc., pp. 49-53.
Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.
Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.
Stone, Gregg W., M.D. et al., "Fenoldopam Mesylate for the Prevention of Contrast-Induced Nephropathy," JAMA Nov. 5, 2003, vol. 290, No. 17, ©2003 American Medical Association, pp. 2284-2291.
Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

(56) References Cited

OTHER PUBLICATIONS

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.
Tay, Victoria KM et al., "Computed tomography fluoroscopy-guided chemical lumbar sympathectomy: Simple, safe and effective," Oct. 31, 2001, Diagnositc Radiology, Australasian Radiology 2002, vol. 46, pp. 163-166.
Thompson, Gregory W. et al, "Bradycardia Induced by Intravascular Versus Direct Stimulation of the Vagus Nerve," Aug. 24, 1997, The Society of Thoracic Surgeons 1998, pp. 637-642.
Thrasher, Terry N., "Unloading arterial baroreceptors causes neurogenic hypertension," Dec. 4, 2001, Am J Physiol Regulatory Integrative Comp. Physiol., vol. 282, ©2002 the American Physiological Society, pp. R1044-R1053.
Tokuno, Hajime A. et al., "Local anesthetic effects of cocaethylene and isopropylcocaine on rat peripheral nerves," Oct. 7, 2003, Brain Research 996, 2004, © 2003 Elsevier B.V., pp. 159-167.
Trapani, Angelo J. et al., "Neurohumoral interactions in conscious dehydrated rabbit," Am J Physiol 1988, vol. 254, ©1988 the American Physiological Society, pp. R338-R347.
Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.
Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.
Trumble, Dennis R., and James A. Magovern, "Comparison of Dog and Pig Models for Testing Substernal Cardiac Compression Devices," Nov. 2003, ASAIO Journal 2004, pp. 188-192.
Tsai, E., "Intrathecal drug delivery for pain indications, technique, results," Pain Lecture presentation, Jun. 8, 2001, 31 pages.
Uematsu, Toshihiko, M.D., Ph.D., F.I.C.A. et al., "Extrinsic Innervation of the Canine Superior Vena Cava, Pulmonary, Portal and Renal Veins," Angiology-Journal of Vascular Diseases, Aug. 1984, pp. 486-493.
United States Renal Data System, "USRDS 2003 Annual Data Report: Atlas of End-Stage Renal Disease in the United States," National Institutes of Health, National Institute of Diabetes and Digestive and Kidney Diseases, 2003, 593 pages.
Valente, John F. et al., "Laparoscopic renal denervation for intractable ADPKD-related pain," Aug. 24, 2000, Nephrology Dialysis Transplantation 2001, vol. 16, European Renal Association-European Dialysis and Transplant Association, p. 160.
Van Antwerp, Bill and Poonam Gulati., "Protein Delivery from Mechanical Devices Challenges and Opportunities," Medtronic Presentation, 19 pages.
Velazquez, Eric J., "An international perspective on heart failure and left ventricular systolic dysfunction complicating myocardial infarction: the VALIANT registry," Aug. 5, 2004, European Heart Journal, vol. 25, ©2004 Elsevier Ltd., pp. 1911-1919.
Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, ©2003 American College of Cardiology Foundation, pp. 1605-1610.
Villarreal, Daniel et al., "Effects of renal denervation on postprandial sodium excretion in experimental heart failure," Oct. 29, 1993, Am J Physiol 266, 1994, pp. R1599-R1604.
Villarreal, Daniel et al., "Neurohumoral modulators and sodium balance in experimental heart failure," Nov. 6, 1992, Am J Physiol, vol. 264, 1993, pp. H1187-H1193.
Wagner, C.D. et al, "Very low frequency oscillations in arterial blood pressure after autonomic blockade in conscious dogs," Feb. 5, 1997, Am J Physiol Regul Integr Comp Physiol 1997, vol. 272, ©1997 the American Physiological Society, pp. 2034-2039.
Wald, Jan D. Ph.D. et al., "Cardiology Update 2003," Sep. 11, 2003, © 2003 AG Edwards, 120 pages.
Wang, Xi et al., "Alterations of adenylyl cyclase and G proteins in aortocaval shut-induced heart failure," Jul. 2004, Am J Physiol Heart Circ Physiol., vol. 287, ©2004 the American Physiological Society, pp. H118-H125.
Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.
Weiner, Richard L., M.D., "Peripheral nerve neurostimulation," Neurosurgery Clinics of North America 2003, vol. 14, ©2003 Elsevier Inc., pp. 401-408.
Weisbord, Steven D., M.D. and Paul M. Palevsky, M.D., "Radiocontrast-Induced Acute Renal Failure," Jul. 10, 2004, Journal of Intensive Care Medicine 2005, vol. 20 (2), ©2005 Sage Publications, pp. 63-75.
Wolinsky, Harvey, M.D., Ph.D. and Swan N. Thung, M.D., "Use of a Perforated Balloon Catheter to Deliver Concentrated Heparin Into the Wall of the Normal Canine Artery," Aug. 30, 1989, JACC 1990, vol. 15, © 1990 The American College of Cardiology, pp. 475-481.
Wyss, J.Michael et al., "Neuronal control of the kidney: Contribution to hypertension," Apr. 8, 1991, Can. J. Physiol. Pharmacol., vol. 70, 1992, pp. 759-770.
Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [HIJAMI] Registry)," Feb. 24, 2004, The American Journal of Cardiology, vol. 93, Jun. 15, 2004, ©2004 by Excerpta Medica, Inc., pp. 1526-1528.
Ye, Richard D., M.D., Ph.D., "Pharmacology of the Peripheral Nervous System," E-425 MSB, 6 pages.
Ye, Shaohua et al., "Renal Injury Caused by Intrarenal Injection of Phenol Increases Afferent and Efferent Renal Sympathetic Nerve Activity," Mar. 12, 2002, American Journal of Hypertension Aug. 2002, vol. 15, No. 8, ©2002 the American Journal of Hypertension, Ltd. Published by Elsevier Science Inc., pp. 717-724.
Yong-Quan, Dong et al., "The therapeutic effect of pulsed electric field on experimental spinal cord injury," Beijing Army General Hospital of People's Liberation Army, Beijing, 5 pages (full article in Chinese; abstract on last page).
Young, James B., M.D., Facc, "Management of Chronic Heart Failure: What Do Recent Clinical Trials Teach Us?" Reviews in Cardiovascular Medicine 2004, vol. 5, Suppl. 1, ©2004 MedReviews, LLC, pp. S3-S9.
Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.
Zimmermann, Ulrich, "Electrical Breakdown, Electropermeabilization and Electrofusion," Rev. Physiol. Biochem. Pharmacol., vol. 105, ©Springer-Verlag 1986, pp. 175-256.
Zucker, Irving H. et al., "The origin of sympathetic outflow in heart failure: the roles of angiotensin II and nitric oxide," Progress in Biophysics & Molecular Biology 2004, vol. 84, ©2003 Elsevier Ltd., pp. 217-232.
Zundert, Jan Van, M.D. Fipp and Alex Cahana, M.D. Daapm, "Pulsed Radiofrequency in Chronic Pain Management: Looking for the Best Use of Electrical Current," Pain Practice 2005, vol. 5, Issue 2, ©2005 World Institute of Pain, pp. 74-76.
"Cardiac Glycosides," Heart Disease—A Textbook of Cardiovascular Medicine vol. 2, Edited by Eugene Braunwald, 5th Edition, WB Saunders Company, pp. 480-481, 1997.
"Effects of Renal Failure on the Cardiovascular System," 5th Edition Heart Disease, A Textbook of Cardiovascular Medicine, vol. 2, Edited by Eugene Braunwald, W.B. Saunders Company, pp. 1923-1925 1997.
Implantable Pump—The Medtronic MiniMed 2007 Implantable Insulin Pump System, Medtronic MiniMed 2004, 4 pages.
"Renal Parenchymal Disease," Ch. 26, 5th Edition Heart Disease, A Textbook of Cardiovascular Medicine vol. 2, Edited by Eugene Braunwald, WB Saunders Company, pp. 824-825 1997.
Aggarwal, A. et al., Regional sympathetic effects of low-dose clonidine in heart failure. Hypertension. 2003;41:553-7.

(56) References Cited

OTHER PUBLICATIONS

Alexander, B.T. et al., "Renal denervation abolishes hypertension in low-birth-weight offspring from pregnant rats with reduced uterine perfusion," Hypertension, 2005; 45 (part 2): 754-758.
Allen, E.V., "Sympathectomy for essential hypertension," Circulation, 1952, 6:131-140.
Antman, Elliott M. and Eugene Braunwald, "Chapter 37—Acute Myocardial Infarction," Heart Disease—A Textbook of Cardiovascular Medicine, 5th Edition, vol. 2, 1997, Edited by Eugene Braunwald, pp. 1184-1288.
Barajas, L. "Innervation of the renal cortex." Fex Proc. 1978;37:1192-201.
Bhandari, A. and Ellias, M., "Loin pain hematuria syndrome: Pain control with RFA to the Splanchanic plexus," The Pain Clinic, 2000, vol. 12, No. 4, pp. 323-327.
Bichet, D., et al., "Renal intracortical blood flow and renin secretion after denervation by 6-hydroxydopamine." Can J Physiol Pharmacol. 1982;60:184-92.
Bravo, E.L., et al., "Renal denervation for resistant hypertension," American Journal of Kidney Diseases, 2009, 3 pages.
Bunch, Jared T. et al. "Mechanisms of Phrenic Nerve Injury During Radiofrequency Ablation at the Pulmonary Vein Orifice." Journal of Cardiovascular Electrophysiclody. vol. 16, No. 12. pp. 1318-1325. Dec. 2005.
Burns, J. et al., "Relationship between central sympathetic drive and magnetic resonance imaging-determined left ventricular mass in essential hypertension." Circulation. 2007;115:1999-2005.
Campese, V.M. et al., "Renal afferent denervation prevents hypertension in rats with chronic renal failure." Hypertension. 1995;25:878-82.
Campese, V.M., "Neurogenic factors and hypertension in renal disease." Kidney Int. 2000;57 Suppl 75:S2-3.
Chen, S.A. et al., "Initiation of atrial fibrillation by ectopic beats originating from the pulmonary veins: electrophysiological characteristics, pharmacological responses, and effects of radiofrequency ablataion," Circulation, 1999, 100:1879-1886.
Chin, J.L. et al., "Renal autotransplantation for the loin pain-hematuria syndrome: long term follow up of 26 cases," J Urol, 1998, vol. 160, pp. 1232-1236.
Curtis, J.J. et al., "Surgical theray for persistent hypertension after renal transplantation," Transplantation, 1981, 31(2):125-128.
Devereaux, R.B. et al., "Regression of Hypertensive Left Ventricular Hypertrophy by Losartan Compared With Atenolol: The Losartan Intervention for Endpoint Reduction in Hypertension (LIFE) Trial," Circulation, 2004, vol. 110, pp. 1456-1462.
Dibona, Gerald F., L.L. Sawin, Effect of renal nerve stimulation on NaCI and H2O transport in Henle's loop of the rat,: 1982, American Physiological Society, F576-F580, 5 pages.
Esler, M. et al., "Mechanism of elevated plasma noradrenaline in the course of essential hypertension." J Cardiovasc Pharmacol. 1986;8:S39-43.
Esler, M. et al., "Noradrenaline release and the pathophysiology of primary human hypertension." Am J Hypertens. 1989; 2:140S-146S.
Esler, M. et al., "Sympathetic nerve biology in essential hypertension," Clin and Exp Pharmacology and Physiology, 2001, 28:986-989.
European Examination Report; European Patent Application No. 07799148.7; Applicant: Ardian, Inc.; Date of Mailing: Jan. 19, 2010, 4 pages.
European Examination Report; European Patent Application No. 09156661.2; Applicant: Ardian, Inc.; Date of Mailing: Jan. 19, 2010, 6 pages.
European Search Report; European Patent Application No. 07798341.9; Applicant: Ardian, Inc.; Date of Mailing Aug. 4, 2011; 6 pages.
Evelyn, K.A. et al., "Effect of thoracolumbar sympathectomy on the clinical course of primary (essential) hypertension," Am J Med, 1960;28:188-221.
Ex parte Quayle Office Action; U.S. Appl. No. 11/144,173; Mailed on May 28, 2009, 4 pages.
Fajardo, J. et al., Effect of chemical sympathectomy on renal hydroelectrolytic handling in dogs with chronic caval constriction. Clin Physiol Biochem. 1986;4:252-6.
Final Office Action; U.S. Appl. No. 11/233,814; Mailed on Jan. 29, 2009, 11 pages.
Final Office Action; U.S. Appl. No. 11/266,993; Mailed on Jan. 8, 2010, 7 pages.
Final Office Action; U.S. Appl. No. 11/363,867; Mailed on May 1, 2009, 8 pages.
Final Office Action; U.S. Appl. No. 11/451,728; Mailed on Jan. 13, 2009, 7 pages.
Final Office Action; U.S. Appl. No. 11/599,649; Mailed on Jan. 15, 2009, 10 pages.
Final Office Action; U.S. Appl. No. 11/599,723; Mailed on Apr. 5, 2010, 17 pages.
Final Office Action; U.S. Appl. No. 11/599,890; Mailed on Apr. 29, 2009, 9 pages.
Fuster, Valentin et al. "ACC/AHA/ESC Practice Guidelines: ACA/AHA/ESC 2006 Guidelines for the Management of Patients with Atrial Fibrillation." JACC vol. 48, No. 4, Aug. 15, 2006.
Gazdar, A.F. and G.J. Dammin, "Neural degeneration and regeneration in human renal transplants," NEJM, Jul. 30, 1970, 283:222-244.
Getts, R.T. et al., "Regression of left ventricular hypertrophy after bilateral nephrectomy," Nephrol Dial Transplant, 2006, vol. 21, pp. 1089-1091.
Gottschalk, C.W., "Renal nerves and sodium excretion," Ann. Rev. Physiol., 1979, 41:229-240.
Haissaguerre, M. et al., "Spontaneous initiation of atrial fibrillation by ectopic beats orginating in the pulmonary veins," New England Journal of Medicine, 1998, 339: 659-666.
Hampers, C.L. et al., "A hemodynamic evaluation of bilateral nephrectomy and hemodialysis in hypertensive man," Circulation. 1967;35:272-288.
Hansen, J.M. et al., "The transplanted human kidney does not achieve functional reinnervation," Clin Science, 1994, vol. 87, pp. 13-20.
Hasking, G.J. et al., "Norepinephrine spillover to plasma in patients with congestive heart failure: evidence of increased overall and cardiorenal sympathetic nervous activity." Circulation. 1986;73:615-21.
Hausberg, M. et al., "Sympathetic nerve activity in end-stage renal disease," Circulation, 2002, 106: 1974-1979.
Heuer, G.J., "The surgical treatment of essential hypertension," Annals of Surgery, 1936; 104 (4): 771-786.
International Search Report, PCT/US02/0039, Mailed Sep. 11, 2002, Applicant: Advanced Neuromodulation Systems, Inc.
International Search Report, PCT/US02/25712, Mailed on Apr. 23, 2003, Applicant: Cyberonics, Inc.
International Search Report, PCT/US03/08014, Mailed on Sep. 23, 2003, Applicant: The General Hospital Corporation.
International Search Report, PCT/US03/09764, Mailed on Oct. 28, 2003, Applicant: CVRX, Inc.
Joles, J.A. et al., "Causes and Consequences of Increased Sympathetic Activity in Renal Disease." Hypertension. 2004;43:699-706.
Kassab, S. et al., "Renal denervation attenuates the sodium retention and hypertension associated with obesity," Hypertension, 1995, 25:893-897.
Katholi, R.E. et al., "Importance of the renal nerves in established two-kidney, one clip Goldblatt hypertension," Hypertension, 1982, 4 (suppl II): II-166-II-174.
Katholi, R.E. et al., "Role of the renal nerves in the pathogenesis of one-kidney renal hypertension in the rat," Hypertension, 1981, 3(4) 404-409.
Katholi, R.E., "Renal nerves and hypertension: an update," Fed Proc., 1985, 44:2846-2850.
Kaye, D.M. et al., "Functional and neurochemical evidence for partial cardiac sympathetic reinnervation after cardiac transplantation in humans," Circulation, 1993, vol. 88, pp. 1101-1109.
Kirchheim, H. et al., "Sympathetic modulation of renal hemodynamics, renin release and sodium excretion," Klin Wochenschr, 1989, 67:858-864.
Klein, K. et al., "Impaired autofeedback regulation of hypothalamic norepinephrine release in experimental uremia." J Am Soc Nephrol. 2005;16:2081-7.

(56) References Cited

OTHER PUBLICATIONS

Koomans, H.A., et al., "Sympathetic hyperactivity in chronic renal failure: a wake-up call." J Am Soc Nephrol. 2004;15:524-37.
Kopp, U. et al., "Dietary sodium loading increases arterial pressure in afferent renal-denervated rats," Hypertension, 2003, 42:968-973.
Kopp, U.C. et al., "Renal sympathetic nerve activity modulates afferent renal nerve activity by PGE2-dependent activation of alpha1- and alpha2-adrenoceptors on renal sensory nerve fibers." Am J Physiol Regul Integr Comp Physiol. 2007;293:R1561-72.
Kumagai, K. et al. "New Approach to Pulmonary Vein Isolation for Atrial Fibrillation Using a Multielectrode Basket Catheter." Circulation Journal. 2006;70:88-93.
Le Noble, J.L. et al., "Pharmacological evidence for rapid destruction of efferent renal nerves in rats by intrarenal infusion of 6-hydroxydopamine." J Hypertens Suppl. 1985;3:S137-40.
Lee, Michael A. (editor). SPORTSMed. Connecticut State Medical Society Committee on the Medical Aspects of Sports. Fall/Winter 2005. 10 pages.
Lenoble, L.M. et al., "Selective efferent chemical sympathectomy of rat kidneys." Am J Physiol. 1985;249:R496-501.
Luippold, G. et al., "Chronic renal denervation prevents glomerular hyperfiltration in diabetic rats," Nephrol Dial Transplant (2004) 19:342-347.
Mancia, G., Grassi, G., Giannattasio, C., Seravalle, G., "Sympathetic activation of pathogenesis of hypertension and progression of organ damage," Hypertension 1999, 34 (4 Pt 2): 724-728.
Morrisey, D.M. et al., "Sympathectomy in the treatment of hypertension: Review of 122 cases," Lancet. 1953;1:403-408.
Non-Final Office Action; U.S. Appl. No. 10/408,665; Mailed on Mar. 21, 2006, 14 pages.
Non-Final Office Action; U.S. Appl. No. 11/129,765; Mailed on Oct. 6, 2006, 30 pages.
Non-Final Office Action; U.S. Appl. No. 11/129,765; Mailed on May 18, 2007, 10 pages.
Non-Final Office Action; U.S. Appl. No. 11/129,765; Mailed on Sep. 10, 2007, 5 pages.
Non-Final Office Action; U.S. Appl. No. 11/144,173; Mailed on Apr. 5, 2007, 33 pages.
Non-Final Office Action; U.S. Appl. No. 11/144,173; Mailed on Sep. 10, 2007, 5 pages.
Non-Final Office Action; U.S. Appl. No. 11/144,298; Mailed on Apr. 5, 2007, 33 pages.
Non-Final Office Action; U.S. Appl. No. 11/144,298; Mailed on Sep. 10, 2007, 5 pages.
Non-Final Office Action; U.S. Appl. No. 11/144,298; Mailed on Dec. 29, 2008, 7 pages.
Non-Final Office Action; U.S. Appl. No. 11/144,298; Mailed Oct. 29, 2009, 8 pages.
Non-Final Office Action; U.S. Appl. No. 11/145,122; Mailed on Apr. 11, 2007, 33 pages.
Non-Final Office Action; U.S. Appl. No. 11/145,122; Mailed on Sep. 10, 2007, 5 pages.
Non-Final Office Action; U.S. Appl. No. 11/189,563; Mailed on May 28, 2009, 5 pages.
Non-Final Office Action; U.S. Appl. No. 11/233,814; Mailed on Jun. 17, 2008, 12 pages.
Non-Final Office Action; U.S. Appl. No. 11/252,462; Mailed on Feb. 22, 2010, 6 pages.
Non-Final Office Action; U.S. Appl. No. 11/266,993; Mailed on Dec. 30, 2008, 7 pages.
Non-Final Office Action; U.S. Appl. No. 11/266,993; Mailed on Jul. 8, 2009, 5 pages.
Non-Final Office Action; U.S. Appl. No. 11/363,867; Mailed on Sep. 25, 2008, 10 pages.
Non-Final Office Action; U.S. Appl. No. 11/368,553; Mailed on Oct. 7, 2009, 5 pages.
Non-Final Office Action; U.S. Appl. No. 11/368,553; Mailed on May 18, 2010, 4 pages.
Non-Final Office Action; U.S. Appl. No. 11/368,809; Mailed on Dec. 3, 2009, 4 pages.
Non-Final Office Action; U.S. Appl. No. 11/368,949; Mailed on Jun. 11, 2010, 6 pages.
Non-Final Office Action; U.S. Appl. No. 11/368,971; Mailed on Aug. 24, 2010, 9 pages.
Non-Final Office Action; U.S. Appl. No. 11/451,728; Mailed on Jun. 12, 2008, 41 pages.
Non-Final Office Action; U.S. Appl. No. 11/451,728; Mailed on Jul. 2, 2009, 5 pages.
Non-Final Office Action; U.S. Appl. No. 11/451,728; Mailed on Dec. 28, 2009, 7 pages.
Non-Final Office Action; U.S. Appl. No. 11/504,117; Mailed on Mar. 31, 2009, 10 pages.
Non-Final Office Action; U.S. Appl. No. 11/599,649; Mailed on Jun. 23, 2008, 9 pages.
Non-Final Office Action; U.S. Appl. No. 11/599,649; Mailed on Mar. 30, 2009, 10 pages.
Non-Final Office Action; U.S. Appl. No. 11/599,723; Mailed on Jun. 26, 2009, 17 pages.
Non-Final Office Action; U.S. Appl. No. 11/688,178; Mailed on Jun. 28, 2010, 5 pages.
Non-Final Office Action; U.S. Appl. No. 11/840,142; Mailed on Apr. 3. 2009, 13 pages.
Non-Final Office Action; U.S. Appl. No. 12/567,521; Mailed on Sep. 3, 2010, 9 pages.
Non-Final Office Action; U.S. Appl. No. 12/616,708; Mailed Sep. 16, 2010, 10 pages.
Non-Final Office Action; U.S. Appl. No. 12/725,375; Mailed on Oct. 12, 2010, 14 pages.
Non-Final Office Action; U.S. Appl. No. 11/599,723; Mailed on Oct. 15, 2010, 16 pages.
O'Hagan, K.P. et al., "Renal denervation decreases blood pressure in DOCA-treated miniature swine with established hypertension," Am J Hypertens., 1990, 3:62-64.
Onesti, G. et al., "Blood pressure regulation in end-stage renal disease and anephric man," Circ Res Suppl., 1975, 36 & 37: 145-152.
Page, I.H. et al., "The Effect of Renal Denervation on the Level of Arterial Blood Pressure and Renal Function in Essential Hypertension." J Clin Invest. 1935;14:27-30.
Pappone, Carol and Santinelli, Vincenzo. "Multielectrode basket catheter: A new tool for curing atrial fibrillation?" Heart Rhythm, vol. 3, Issue 4, pp. 385-386. Apr. 2006.
Petersson, M. et al., "Long-term outcome in relation to renal sympathetic activity in patients with chronic heart failure." Eur Heart J. 2005;26:906-13.
Pitt, B. et al., "Effects of Eplerenone, Enalapril, and Eplerenone/Enalapril in Patients With Essential Hypertension and Left Ventricular Hypertrophy: The 4E-Left Ventricular Hypertrophy Study," Circulation, 2003, vol. 108, pp. 1831-1838.
Pope, Jill. "Fixing a Hole: Treating Injury by Repairing Cells." The New York Academy of Sciences. Jul. 6, 2006. 6 pages.
Schlaich, M.P. et al., Relation between cardiac sympathetic activity and hypertensive left ventricular hypertrophy. Circulation. 2003;108:560-5.
Schlaich, M.P. et al., "Sympathetic augmentation in hypertension: role of nerve firing, norepinephrine reuptake, and angiotensin neuromodulation," Hypertension, 2004, 43:169-175.
Shah, D.C., Haissaguerre, M., Jais, P., "Catheter ablation of pulmonary vein foci for atrial fibrillation: pulmonary vein foci ablation for atrial firbrillation," Thorac Cardiovasc Surg, 1999, 47 (suppl. 3): 352-356.
Shannon, J.L. et al., "Studies on the innervation of human renal allografts," J Pathol. 1998, vol. 186, pp. 109-115.
Shlipak, M.G. et al., "The clinical challenge of cardiorenal syndrome." Circulation. 2004;110:1514-7.
Smithwick, R.H., "Surgical treatment of hypertension," Am J Med 1948, 4:744-759.
Smithwick, R.H. et al., "Hypertension and associated cardiovascular disease: comparison of male and female mortality rates and their influence on selection of therapy," JAMA, 1956, 160:1023-1033.
Smithwick, R.H. et al., "Splanchnicectomy for essential hypertension," Journal Am Med Assn, 1953;152:1501-1504.

(56) References Cited

OTHER PUBLICATIONS

Strojek, K. et al., "Lowering of microalbuminuria in diabetic patients by a sympathicoplegic agent: novel approach to prevent progression of diabetic nephropathy?" J Am Soc Nephrol. 2001;12:602-5.
Thatipelli et al., CT Angiography of Renal Artery Anatomy for Evaluating Embolic Protection Devices, Journal of Vascular and Interventional Radiology, Jul. 2007, pp. 842-846.
Vonend, O. et al., "Moxonidine treatment of hypertensive patients with advanced renal failure." J Hypertens. 2003;21:1709-17.
Whitelaw, G.P., Kinsey, D., Smithwick, R.H., "Factors influencing the choice of treatment in essential hypertension: surgical, medical, or a combination of both," Am J Surg, 1964, 107:220-231.
Ye, S. et al., "A limited renal injury may cause a permanent form of neurogenic hypertension." Am J Hypertens. 1998;11:723-8.
Zanchetti, A. et al., "Practice Guidelines for Primary Care Physicians: 2003 ESH/ESC Hypertension Guidelines," Journal of Hypertension, vol. 21, No. 10, 2003, pp. 1779-1786.
Zanchetti, A.S., "Neural regulation of renin release: Experimental evidence and clinical implications in arterial hypertension," Circulation, 1977, 56(5) 691-698.
Zoccali, C. et al., "Plasma norepinephrine predicts survival and incident cardiovascular events in patients with end-stage renal disease." Circulation. 2002;105:1354-9.
Cahana, A. et al., "Acute Differential Modulation of Synaptic Transmission and Cell Survival During Exposure to Pulsed and Continuous Radiofrequency Energy," The Journal of Pain, May 2003, pp. 197-202, vol. 4, No. 4, © 2003 by the American Pain Society.
Heida, T., et al., "Investigating Membrane Breakdown of Neuronal Cells Exposed to Nonuniform Electric Fields by Finite-Element Modeling and Experiments," IEEE Transactions on Biomedical Engineering, vol. 49, No. 10, Oct. 2002, pp. 1195-1203.
Lee, R. C., et al., "Biophysical Injury Mechanisms in Electrical Shock Trauma," Annu. Rev. Biomed. Eng., 2000. 02:477-509, Copyright © 2000 by Annual Reviews.
Podhajsky, R. J., et al. "The Histologic Effects of Pulsed and Continuous Radiofrequency Lesions at 42° C to Rat Dorsal Root Ganglion and Sciatic Nerve," SPINE, vol. 30, No. 9, pp. 1008-1013, Lippincott Williams & Wilkins Inc, 2005.
U.S. Appl. No. 11/133,925, May 20, 2005, Gelfand.
U.S. Appl. No. 11/233,814, Denise Demarais.
U.S. Appl. No. 11/252,462, Denise Demarais.
U.S. Appl. No. 11/266,993, Denise Demarais.
U.S. Appl. No. 11/324,188, Denise Demarais.
U.S. Appl. No. 11/363,867, Denise Demarais.
U.S. Appl. No. 11/368,553, Demarais.
U.S. Appl. No. 11/368,577, Demarais.
U.S. Appl. No. 11/368,809, Denise Demarais.
U.S. Appl. No. 11/368,836, Demarais.
U.S. Appl. No. 11/368,949, Denise Demarais.
U.S. Appl. No. 11/368,971, Denise Demarais.
U.S. Appl. No. 95/002,110, filed Aug. 29, 2012, Demarais et al.
U.S. Appl. No. 95/002,209, filed Sep. 13. 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/202,356, filed Sep. 14, 2012, Demarais et al.
Avitall et al., "The creation of linear contiguous lesions in the atria with an expandable loop catheter," Journal of the Americam College of Cardiology, 1999; 33; pp. 972-984.
Benito, F., et al. "Radiofrequency cateheter ablation of accessory pathways in infants." Heart, 78:160-162 (1997).
Dubuc, M., et al., "Feasibility of cardiac cryoablation using a transvenous steerable electrode catheter." J Interv Cardiac Electrophysiol, 2:285-292 (1998).

Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Gelfand, M., et al., "Treatment of renal failure and hypertension." U.S. Appl. No. 60/442,970.
Han, Y.-M, et al., "Renal artery ebolization with diluted hot contrast medium: An experimental study." J Vasc Intery Radiol, 12: 862-868 (2001).
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustrgarten, D.L.,et al., "Cryothermal ablation: Mechanism of tissue injury and current experience in the treatment of tachyarrhythmias." Progr Cardiovasc Dis, 41:481-498 (1999).
Oliverira, V., et al., "Renal denervation normalizes pressure and baroreceptor reflex in high renin hypertension in conscious rats." Hypertension, 19:II-17-II-21 (1992).
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Peet, M., "Hypertension and its Surgical Treatment by bilateral supradiaphragmatic splanchnicectomy" Am J Surgery (1948) pp. 48-68.
Schauerte, P., et al. "Catheter ablation of cardiac autonomic nerves for prevention of vagal atrial fibrillation." Circulation, 102:2774-2780 (2000).
Stella, A., et al., "Effects of reversible renal deneravation on haemodynamic and excretory functions on the ipsilateral and contralateral kidney in the cat." Hypertension, 4.181-188 (1986).
Swartz, J.F., et al., "Radiofrequency endocardial cateheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Weinstock, M., et al., "Renal denervation prevents sodium rentention and hypertension in salt sensitive rabbits with genetic baroreflex impairment." Clinical Science, 90:287-293 (1996).
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardian Electrophysiology, 2001, pp. 401-410.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
U.S. Appl. No. 10/900,199, Jul. 28, 2004, Gelfand.
U.S. Appl. No. 11/129,765, May 13, 2005, Deem.
U.S. Appl. No. 11/144,173, Jun. 3, 2005, Levin et al.
U.S. Appl. No. 11/144,298, Jun. 3, 2005, Levin et al.
U.S. Appl. No. 11/145,122, Jun. 3, 2005, Levin et al.
U.S. Appl. No. 11/189,563, Jul. 25, 2005, Deem.
Augustyniak, R.A. et al., "Sympathetic Overactivity as a Cause of Hypertension in Chronic Renal Failure," Journal of Hypertension, 2002, 20:3-9, Lippincott Williams & Wilkins Press.
Berde, C. et al. "Local Anesthetics," Anesthesia, Chapter 13, 5th addition, pp. 491-521, Churchill-Livingston, Philadelphia 2000.
Blad, B., et al., "An Electrical Impedance index to Assess Electroporation in Tissue," Tissue and Organ (Therapy), pp. 31-34, <http://www.bl.uk> 2001, Oslo.
Braunwald, E., Heart Disease, "A Textbook of Cardiovascular Medicine," 5th Ed., vol. 2, 1997, pp. 480-481, 824-825, 1184-1288 and 1923-1925, W.B. Saunders Company.

(56) References Cited

OTHER PUBLICATIONS

Campese, V.M. et al., "Renal Afferent Denervation Prevents the Progression of Renal Disease in the Renal Ablation Model of Chronic Renal Failure in the Rat," American Journal of Kidney Diseases, Nov. 1995, pp. 861-865, vol. 26, No. 5.

Davalos, R. et al., "Electrical Impedance Tomography for Imaging Tissue Electroporation," IEEE Transactions on Biomedical Engineering, vol. 51, No. 5, May 2004, pp. 761-767, 2004 IEEE.

DiBona, G., "Neural Control of the Kidney: Functionally Specific Renal Sympathetic Nerve Fibers," Am J Physiol Regulatory Integrative Comp Physiol, 2000, 279: R1517-R1524, The American Physiological Society, Bethesda, MD.

DiBona, G.F. et al., Nervous Kidney, "Interaction Between Renal Sympathetic Nerves and the Renin-Angiotensin System in the Control of Renal Function," Hypertension, 2000, 36:1083-1088, American Heart Association, Inc.

DiBona, G.F., "Functionally Specific Renal Sympathetic Nerve Fibers: Role in Cardiovascular Regulation," American Journal of Hypertension, Jun. 2001, 14:163S-170S.

DiBona, G.F., "Sympathetic Nervous System and the Kidney in Hypertension," Current Opinion in Nephrology and Hypertension, 2002, 11:197-200, Lippincott Williams & Wilkins Press.

Dueck, R. et al., "Noninvasive Cardiac Output Monitoring," The Cardiopulmonary and Critical Care Journal, Chest, 120, 2, Aug. 2001, pp. 339-341, American College of Chest Physicians.

Gehl, J. et al., "In Vivo Electroporation of Skeletal Muscle: Threshold, Efficacy and Relation to Electric Field Distribution," Biochimica et Biophysica Acta, 1428, 1999, pp. 233-240, www.elsevier.com/locate/bba <http://www.elsevier.com/locate/bba>.

Hopp, F. A. et al., "Respiratory Responses to Selective Blockade of Carotid Sinus Baroreceptors in the Dog," Am J Physiol Regul Integr Comp Physiol, 1998, 275:10-18, American Physiological Society, Bethesda, MD.

Huang, Wann-Chu et al. "Renal Denervation Prevents and Reverses Hyperinsulinemia-Induced Hypertension in Rats," Hypertension, 1998, 32:249-254, American Heart Association, Inc.

International Search Report, PCT/US04/38498, Mailed Feb. 18, 2005, Applicant: G & L Consulting, LLC (3 pages).

Medrtonic Inc., MiniMed 2007, Implantable Insulin Pump System, Shoreview, MN (4 pages).

Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba <http://www.elsevier.com/locate/bba>.

Nelson, L. et al., "Neurogenic Control of Renal Function in Response to Graded Nonhypotensive Hemorrahage in Conscious Dogs," 1993, pp. R661-R667, American Physiological Society.

Nozawa, T. et al., "Effects of Long Term Renal Sympathetic Denervation on Heart Failure After Myocardial Infarction in Rats," Heart Vessels, 2002, 16:51-56.

Rump, L.C., "The Role of Sympathetic Nervous Activity in Chronic Renal Failure," J Clinical Basic Cardiology, 2001, 4:179-182, Department of Internal Medicine, University of Freiburg, Germany.

Gonschior, P., Comparison of Local Intravascular Drug-Delivery Catheter Systems, Am. Heart J., Dec. 1995, 130:6, 1174-81.

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Oz, Mehmet, Pressure Relief, TIME, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Purerfellner, Helmut et al., Pulmonary Vein Stenosis Following Catheter Ablation of Atrial Fibrillation, Curr. Opin. Cardio. 20 :484-490, 2005.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.

"Iberis—Renal Sympathetic Denervation System: Turning innovation into quality care." [Brochure], Terumo Europe N. V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison Awards ™ " Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul lntegr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global SYMPLICITY registry." EuroIntervention, vol. 9, 2013, 9 pages.

(56) References Cited

OTHER PUBLICATIONS

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gertner, Jon, "Meet the Tech Duo That's Revitalizing the Medical Device Industry." Fast Company, Apr. 15, 2013, 6:00 AM, 17 pages. <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages. <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages. <http://www.medpagetoday.com/Cardiology/PCI/36509>.
Linz, Dominik et al., "Renal denervation suppresses ventricular arrhythmias during acute ventricular ischemia in pigs." Heart Rhythm, vol. 0, No. 0, 2013, 6 pages.
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Millard, F. C., et al, "Renal Embolization for ablation of function in renal failure and hypertension." Postgraduate Medical Journal, 65, 729-734, (1989).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldH eadlines_article&forceid=80880>.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stouffer, G. A. et al., Journal of Molecular and Cellular Cardiology, vol. 62, 2013, 6 pages.
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
European Search Report for App. No. 12189194.9, Mailed Aug. 1, 2013, 11 pages.
Schneider, Peter A., "Endovascular Skills—Guidewire and Catheter Skills for Endovascular Surgery," Second Edition Revised and Expanded, 10 pages, (2003).
Hall, W. H., et al. "Combined embolization and percutaneous radiofrequency ablation of a solid renal tumor." Am. J. Roentgenol,174: 1592-1594 (2000).
Hanson, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988).
Medical-Dictionary.com, Definition of "Animal Model," http://medical-dictionary.com (search "Animal Model"), 2005.
Medtronic, Inc., Annual Report (Form 10-K) (Jun. 28, 2011).
Ong, K. L., et al. "Prevalence, Awareness, Treatment, and Control of Hypertension Among United States Adults 1999-2004." Hypertension, 49: 69-75 (2007) (originally published online Dec. 11, 2006).
Renal Denervation (RDN), Symplicity RDN System Common Q&A (2011), http://www.medtronic.com/rdn/mediakit/RDN%20FAQ.pdf.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Blessing, Erwin et al., Cardiac Ablation and Renal Denervation Systems Have Distinct Purposes and Different Technical Requirements, JACC Cardiovascular Interventions, vol. 6. No. 3, 2013.
ClinicalTrials.gov, Renal Denervation in Patients with uncontrolled Hypertension in Chinese (2011), www.clinicaltrials.gov/ct2/show/NCT01390831.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertenion, Mar. 2013, http://clinicaltrials.gov/ct2/show/NCT01628198.
Prochnau, Dirk et al., Catheter-based renal denervation for drug-resistant hypertension by using a standard electrophysiology catheter; Euro Intervention 2012, vol. 7, pp. 1077-1080.
Schneider, Peter A.., "Endovascular Skills—Guidewires, Catheters, Arteriography, Balloon Angioplasty, Stents",pp. 70-71, 101 and 188-190 (1998).
ThermoCool Irrigated Catheter and Integrated Ablation System, Biosense Webster (2006).

*Figure 13*
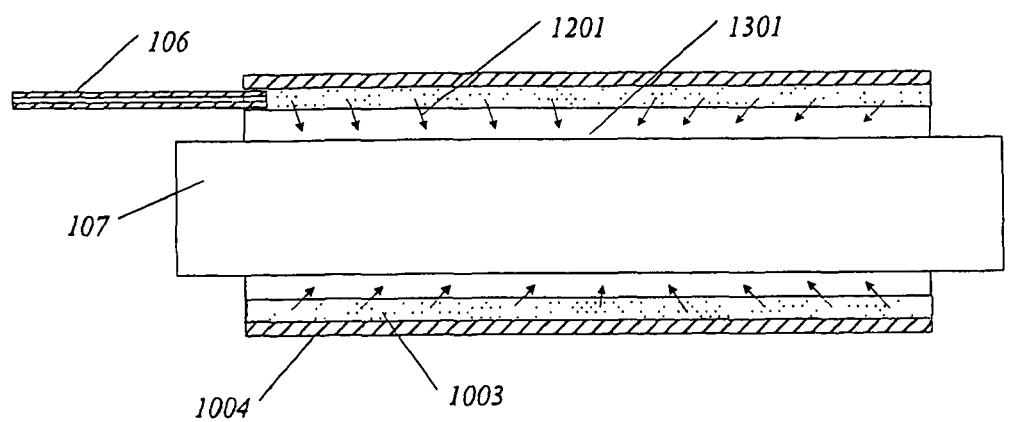
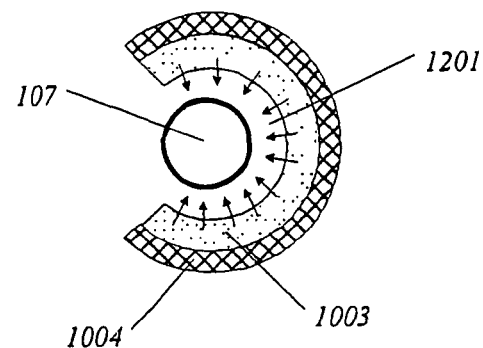
*Figure 14*

METHODS AND DEVICES FOR RENAL NERVE BLOCKING

CROSS-REFERENCE TO RELATED APPLICATIONS

This application is a continuation of U.S. application Ser. No. 10/900,199, filed Jul. 28, 2004, now U.S. Pat. No. 6,978, 174, which is a continuation-in-part of U.S. application Ser. No. 10/408,665, filed Apr. 8, 2003, now U.S. Pat. No. 7,162, 303, which claims priority to the following commonly-owned applications: U.S. Provisional Application No. 60/370,190, filed Apr. 8, 2002, entitled "Modulation Of Renal Nerve To Treat CHF", U.S. Provisional Application No. 60/415,575, filed Oct. 3, 2002, entitled "Modulation Of Renal Nerve To Treat CHF", and U.S. Provisional Application No. 60/442, 970, filed Jan. 29, 2003, entitled "Treatment Of Renal Failure And Hypertension". The disclosure of each application is incorporated herein by reference in its entirety.

FIELD OF THE INVENTION

This invention relates to devices and methods for local drug delivery, and in particular is directed to an implantable system for targeted delivery of a nerve blocking agent to the periarterial space of the renal artery for the purpose of blocking the renal nerve plexus, methods for implanting same, and methods and devices for treating diseases. The invention directs the nerve-blocking agent towards the nerve, prevents dissipation of the agent in the surrounding tissue and provides fixation of the drug delivery mechanism in the surrounding tissue.

BACKGROUND OF THE INVENTION

Hypertension (HTN) and congestive heart failure (CHF) are the most important problems in contemporary cardiology. These chronic diseases account for most cardiovascular morbidity and mortality, and, despite much progress, remain therapeutic challenges. The cornerstone of therapy for both HTN and CHF includes the use primarily oral and intravenous drugs acting directly or indirectly on the kidney, such as angiotensin converting enzyme (ACE) inhibitors and diuretics, with the amount of each drug used dependent on the stage of the disease. While drug therapy is effective in the earliest stages of HTN and CHF, there is no truly effective drug treatment for the mid-to-later stages of these diseases.

HTN and CHF have many different initial causes. Irrespective of initial cause, both diseases follow a common pathway in their progression to end-stage disease, primarily as the result of excessive activity of the renal nerve. It has been shown in accepted animal models that renal denervation can control HTN and improve symptoms and slow down the progression of CHF. However, no drug or device therapies currently exist that can provide long-term, clinically usable blocking of renal nerve activity in humans. The only available clinical method of renal denervation is an invasive surgical procedure, technically difficult and of limited use, as the nerve quickly regenerates.

Of particular significance for this invention is the CHF condition that develops in many patients following a myocardial infarction (MI). Coronary artery disease causes approximately 70% of congestive heart failure. Acute MI due to obstruction of a coronary artery is a common initiating event that can lead ultimately to heart failure. This process by which this occurs is referred to as remodeling and is described in the text Heart Disease, 5th ed., E. Braunwald, Ch. 37 (1997). Remodeling after a myocardial infarction involves two distinct types of physical changes to the size, shape and thickness of the left ventricle. The first, known as infarct expansion, involves a localized thinning and stretching of the myocardium in the infarct zone. This myocardium can go through progressive phases of functional impairment, depending on the severity of the infarction. These phases reflect the underlying myocardial wall motion abnormality and include an initial dyssynchrony, followed by hypokinesis, akinesis, and finally, in cases that result in left ventricular aneurysm, dyskinesis. This dyskinesis has been described as "paradoxical" motion because the infarct zone bulges outward during systole while the rest of the left ventricle contracts inward. Consequently, end-systolic volume in dyskinetic hearts increases relative to nondyskinetic hearts.

The second physical characteristic of a remodeling left ventricle is the attempted compensation of noninfarcted region of myocardium for the infarcted region by becoming hyperkinetic and expanding acutely, causing the left ventricle to assume a more spherical shape. This helps to preserve stroke volume after an infarction. These changes increase wall stress in the myocardium of the left ventricle. It is thought that wall tension is one of the most important parameters that stimulate left ventricular remodeling. In response to increased wall tension or stress, further ventricular dilatation ensues. Thus, a vicious cycle can result, in which dilatation leads to further dilatation and greater functional impairment. On a cellular level, unfavorable adaptations occur as well. This further compounds the functional deterioration.

Takashi Nozawa et al reported the effects of renal denervation in "Effects of long-term renal sympathetic denervation on heart failure after myocardial infarction in rats" published in Heart Vessels (2002) 16:51-56 Springer-Verlag. In rats the bilateral renal nerves were surgically denervated (cut) (RD) two days before MI was induced by coronary artery legation. Four weeks later, left ventricular (LV) function and sodium excretion were determined. In MI rats, RD improved the reduced sodium excretion. MI RD rats revealed lower LV end-diastolic pressure and greater maximum dP/dt as compared with those of MI innervation (INN) rats. LV end-diastolic and end-systolic dimensions were significantly smaller and LV fractional shortening was greater in MI RD rats than in MI INN rats.

Inventors described novel methods and devices for reversible minimally invasive modulation of the renal nerve in copending applications. This application describes novel drug delivery methods and integrated physiological drug delivery and sensing systems that provide a significantly more effective method of blocking the renal nerve for the purpose of treating HTN and CHF than are currently available. The objective of this invention is a fully implantable device that blocks renal nerve activity of at least one kidney that 1) can be placed in a minimally invasive manner and 2) requires minimal intervention by the patient and physician; and will greatly increase patient compliance leading to a higher overall effectiveness of these therapies. In addition, to HTN and CHF, this method may be applicable to other major diseases such as slowing the progression of chronic renal failure and reducing the number of patients requiring chronic hemodialysis.

Nerve blocking in humans is known and practiced mostly in the field of local anesthesia and pain control. While compounds utilized as general anesthetics reduce pain by producing a loss of consciousness, local anesthetics act via a loss of sensation in the localized area of administration in the body. The mechanism by which local anesthetics induce their effect, while not having been determined definitively, is generally thought to be based upon the ability to locally interfere with the initiation and transmission of a nerve impulse, e.g., interfering with the initiation and/or propagation of a depolarization wave in a localized area of nerve tissue. The actions of local anesthetics are general, and any tissue where nerve conduction, e.g., cell membrane depolarization occurs can be affected by these drugs. Thus, nervous tissue mediating both sensory and motor functions can be similarly affected by local anesthetics. Neurotoxins are the chemicals that when applied to nerve tissue in extremely small amounts can block a nerve for a period of time that significantly exceeds that achieved with local anesthetics. They are also more toxic and potentially more dangerous to the patient than local anesthetics.

Different devices and formulations are known in the art for administration of local anesthetics. For example, local anesthetics can be delivered in solution or suspension by means of injection, infusion, infiltration, irrigation, topically and the like. Injection or infusion can be carried out acutely, or if prolonged local effects are desired, localized anesthetic agents can be administered continuously by means of a gravity drip or infusion pump. Thus, local anesthetics such as bupivacaine have been administered by continuous infusion, e.g., for prolonged epidural or intrathecal (spinal) administration. For prolonged control of pain fully implantable pumps have been proposed and implemented. These pumps can store a certain amount of drug and a physician periodically refills those. Several authors proposed drug eluting implants for control of pain and muscle spasms that slowly release an anesthetic agent at the site of implantation.

The duration of action of a local anesthetic is proportional to the time during which it is in actual contact with the nervous tissues. Consequently, procedures or formulations that maintain localization of the drug at the nerve greatly prolong anesthesia. Local anesthetics are potentially toxic, both locally and via systemic absorption, yet must be present long enough to allow sufficient time for the localized pain to subside. Therefore, it is of great importance that factors such as the choice of drug, concentration of drug, and rate and site of administration of drug be taken into consideration when contemplating their use for the application to block renal nerve. Charles Berde in "Mechanisms of Local Anesthetics" (Anesthesia, 5th addition, R. D. Miller, editor, Churchill-Livingstone, Philadelphia 2000, pp. 491-521) stipulated that only 1-2% of the total amount of local anesthetic, when delivered by traditional methods, ever reaches the nerve. The rest of the drug is dissipated by circulation of blood that takes the drug away, not towards the nerve. It is therefore the purpose of this invention to maximize the amount of drug directed towards the nerve so as to achieve the effective blockade of the renal nerve with the minimal amount of drug.

Theoretically, a suitable commercially available implantable drug pump such as a Syncromed pump made by Medtronic Inc. (Shoreview, Minn.) can be used to block the renal nerve in a human. The pump can deliver common commercially available solution of a local anesthetic agent such as bupivacaine to the tissue surrounding the renal nerve via an attached catheter. Although feasible, such embodiment of the renal nerve block will have practical limitations. To block a peripheral nerve (for example, for the purpose of a commonly performed brachial plexus block) using conventional techniques the physician typically infiltrates 10-50 ml of bupivacaine or similar anesthetic into the tissue surrounding the targeted nerve. This usually achieves adequate blocking of both sensory and motor signals for 2 to 6 hours. Commercially available bupivacaine marketed as Marcaine or Sensorcaine is available in concentrations of 0.25 to 0.1%. For peripheral (single nerve) blocks concentrations of 0.5 to 0.75% are typically used. There are several reasons why local anesthetics are so diluted. An amino-amide compound such as bupivacaine can be toxic both locally (it is an irritant) and systemically (it depresses the heart). It is generally perceived that a local anesthetic will not be effective below certain minimum concentration and will be toxic above certain maximum concentration.

Implantable drug pumps are commonly equipped with an internal drug storage reservoir of 30 to 50 ml. Bigger reservoirs are possible but impose severe limitations on the physical and clinical acceptability of the implant. If the continuous (24 hour a day 7 days a week) block of the patient's renal nerve is desired, and a conventional peripheral nerve blocking technique is used, the implanted pump reservoir will need to be refilled every day or even more frequently. This is possible but not practical, since refilling of the pump is associated with the skin puncture, causing pain and leading to the risk of local and systemic infection. Also, daily infusion of a large amount of drug can result in a serious risk to the patient's health, especially if the patient has a weak heart. Notably the same drug bupivacaine is effective in a much lower doze when delivered directly to the targeted nerve tissue in the patient's spine. For example, an effective intrathecal (spinal) pain block can be achieved with 2-5 ml of bupivacaine. This observation shows that more targeted delivery of the same drug to the nerve tissue can result in 10 times or more reduction of the amount of drug needed for nerve blocking.

It is therefore the purpose of this invention to provide novel methods and implantable devices that will effectively block renal nerve by targeting the delivery of the selected drug to the nerve, reducing dissipation of the drug into the surrounding tissue, reducing the amount of drug stored in the device and increasing the time interval between the refilling or replacement of the device. It is also the purpose of this invention to enable testing of the effectiveness of the renal nerve blockade and to perform the renal block automatically, intermittently and/or periodically in the clinical scenarios where the continuous block is not desired.

SUMMARY OF THE INVENTION

Surgical denervation of the kidney in experimental animals suggested multiple immediate and long-term benefits for patients with cardiac and renal diseases. The most significant potential beneficial effects are: slowing of the progression of CHF, resolution of fluid overload in CHF by induction or enhancement of diuresis, reduction of remodeling after a myocardial infarct, reduction of hypertension and slowing of the progression of chronic renal disease to dialysis. The benefits are achieved via the reduction of the systemic sympathetic tone causing vasoconstriction of blood vessels, reduction of the load on the heart and the direct effects of denervation on the kidney. Both single kidney denervation and bilateral denervation have potential benefits. Surgical denervation has been previously performed in animals and in few humans to control pain. It requires a major surgery and is ineffective in long term, since renal nerves eventually grow back. Additionally, after the surgical denervation, the renal nerve can re-grow in a pathological way and can cause pain and other serious side effects. Since fibrotic changes at the site of denervation make repeat surgical denervation impossible, patients face the possibility of the removal of the kidney to control the pain.

The inventors suggest an alternative method of reducing or blocking the renal nerve activity in patients by minimally invasive renal nerve modulation. Renal nerve modulation is achieved by controlled infusion of a nerve-blocking agent into the periarterial space of the renal artery of the kidney. The periarterial space is the area surrounding the renal arteries and veins, extending from the aorta and vena cava to and including the area around the kidney itself. Since renal nerves follow the external surface of the renal artery, when an effective concentration of the nerve-blocking agent is present in this periarterial space, the renal nerve activity is substantially reduced or stopped. Methods and devices for both continuous and intermittent periodic blocking of the renal nerve are proposed. These methods and devices provide effective, reversible nerve blocking for a clinically relevant duration of time, while avoiding major surgery and irreparable damage to the nerve that characterize the previously used surgical denervation.

The preferred embodiment devices can be implantable drug pumps or drug eluting implants. Both classes of local drug delivery devices are known. Implanted pumps have been successfully used previously for control of pain by infusion of local anesthetics into the patient's spine. Implantable pumps range from simple reservoirs (ports) implanted under the skin with an attached catheter to sophisticated microprocessor driven programmable devices similar to pacemakers. Drug eluting implants have been used to deliver birth control agents and to prevent restenosis of coronary arteries.

Implanted pumps can also be refilled with drug without surgery using a transdermal port accessible with a needle, though it is preferable to extend the time between refillings to minimize pain and the risk of infection. The programmable implantable pump embodiment also has an advantage of the periodic drug delivery that can be adjusted up or down using a remote communication link. This is particularly significant in treatment of chronic diseases such as CHF where the continuous constant nerve blocking can result in adaptation (resting of the physiologic gain or compensation) and the loss of therapeutic effect.

Drug eluting implants work primarily by diffusion. Drug eluting implants are advantageous in the treatment of a temporary condition such as infarct expansion following acute MI where an implant that blocks the nerve for approximately 30 days and then dissolves on its own can be the best embodiment of the invention.

SUMMARY OF THE DRAWINGS

A preferred embodiment and best mode of the invention is illustrated in the attached drawings that are described as follows:

FIG. 13 illustrates the drug infusion catheter that overlaps the renal artery and directs the drug infusion towards the renal nerve.

FIG. 14 is a cross-sectional view of the catheter and artery shown in FIG. 13.

DETAILED DESCRIPTION OF THE INVENTION

Figure 1:
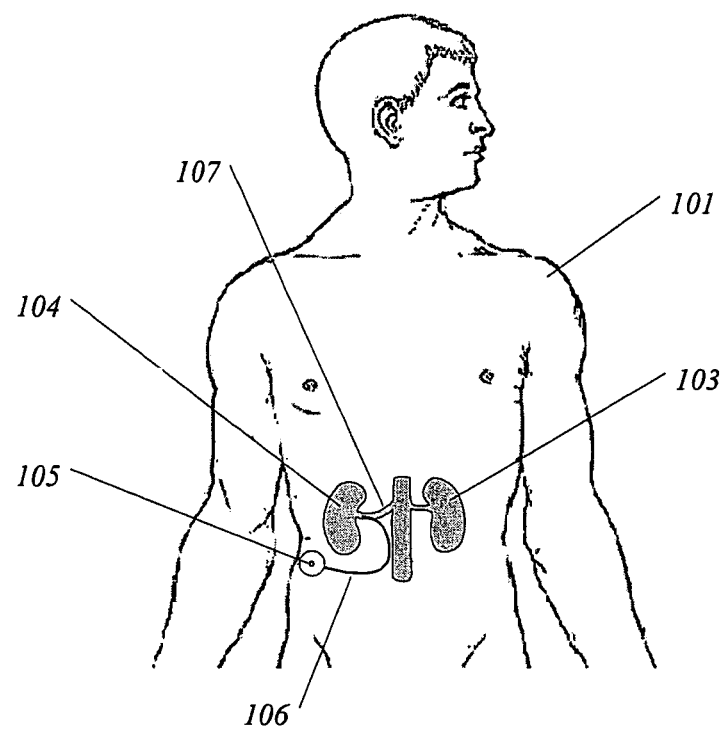
FIG. 1 illustrates the patient treated with an implanted pump embodiment of the invention.

For the proposed clinical use, the capability of the invention is to block the sympathetic activity of the renal nerve of the kidney by controlled local delivery of a nerve-blocking agent with the goal of improving the patient's renal and cardiac function. Elements of the invention are useful for blocking nerves for the purpose other than treating cardiorenal disease and can be applied in other anatomic locations.

A nerve blocking agent is a drug that reduces or blocks conduction of signals by renal nerves. The nerve blocking agents used can be selected from different groups including (1) local anesthetics, (2) ketamine (a well known sedative with nerve blocking properties), (3) tricyclic antidepressants such as amitriptyline, (4) neurotoxins such as tetrodotoxin and saxitoxin or (5) any other class or type of agent that transiently or permanently, partially or completely alters nerve conduction. The terms nerve blocking agent and nerve blocking drug are interchangeable.

Cardiorenal disease is defined as a condition, chronic or acute, that involves both the heart and the kidney. Examples of cardiorenal diseases are hypertension and CHF. Cardiorenal diseases are characterized by the elevated activity of the renal nerve.

For the purpose of this invention, the renal nerve is defined as any individual nerve or plexus of nerves and ganglia that conducts a nerve signal to and/or from the kidney and is anatomically located on the surface of the renal artery, parts of aorta where the renal artery branches from the aorta and/or on branches of the renal artery. The renal nerve generally enters the kidney in the area of the hilum of the kidney, but may enter in any location where a renal artery or branch of the renal artery enters the kidney.

Periarterial space is defined as the space immediately surrounding the renal arteries, renal veins and their branches between the aorta and the hilum of the kidney. The renal fat pad is defined as the adipose tissue or fat that fills the periarterial space and surrounds the renal artery, renal vein, renal nerves and the kidney itself. The renal fascia is the layer of connective tissue that surrounds, envelopes and contains the renal artery, renal vein, renal fatpad and the kidney itself.

An implantable or implanted device (commonly termed an "implant") is an artificial device fully enclosed in the patient's body. It is significant that implants allow the natural skin of the patient to serve as a barrier against infection. An implant can be, for example, a complex electromechanical pump, catheter and port or a drug-releasing polymer. Implantation can be achieved by open surgery, minimally invasive surgery or a transcatheter intervention, whether extravascular, intravascular or combination of any of the above. During the implantation procedure, a surgical instrument or catheter is used to cross the skin, penetrating into the patient's body. The implant is positioned at the desired site and the pathway used to access the site is closed. The site heals and the device is now fully implanted.

An implantable pump is an implantable device that is inserted under the patient's skin and can be refilled using a transdermal needle access. An implantable pump may have an integral catheter or can be equipped with a separate catheter that delivers medication to the periarterial space. Depending on the desired treatment modality, a preferred implantable pump can be programmable, patient controlled or a constant rate device.

A drug eluting implant is a device that is fully implanted in the body that slowly elutes the nerve-blocking agent into the target space. One example of such a space is the renal periarterial space. Another example is inside the renal capsule, or the virtual space between the kidney tissue and the fibrous sheath surrounding the kidney tissues itself. Drug eluting implants work by diffusion and can be biodegradable or not. An osmotic pump is also a drug eluting implant. Different matrixes that serve to slow down the diffusion of the drug into a target space are all called drug eluting implants for the purpose of this invention. These include gels, patches, injectable microspheres, suspensions, solutions or any other matrix that may hold sufficient drug to cause the intended effect.

FIG. 1 illustrates a patient 101 treated with the preferred embodiment of the invention. Patient has kidneys 103 and 104 that are bean shaped organs 12 cm long, 6 cm wide, 3 cm thick located outside and behind the peritoneal cavity. Patient is equipped with an implantable drug pump 105 implanted in the patient's side under the skin. The pump is equipped with a drug delivery catheter 106 that terminates in the area of the renal artery 107 where the delivered drug is capable of blocking the renal nerve.

Figure 2:
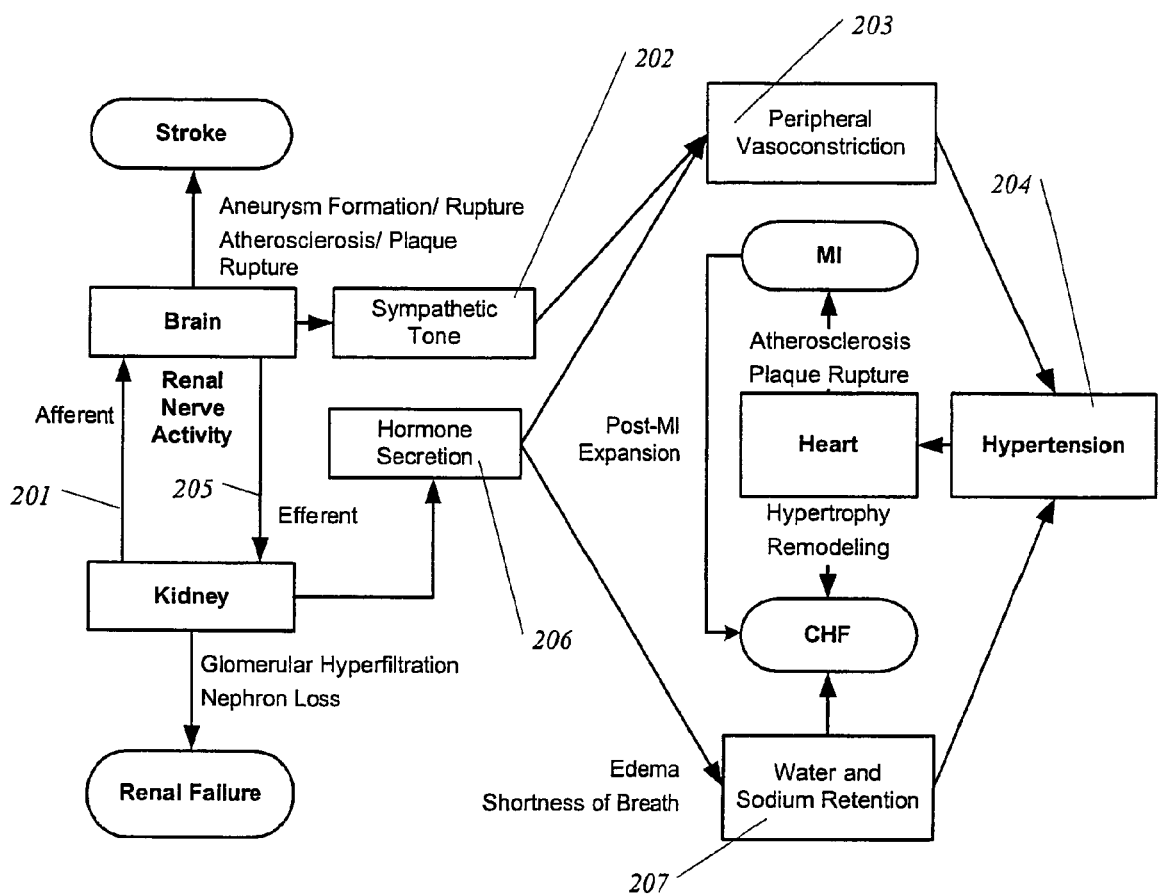
FIG. 2 illustrates the physiologic mechanisms of renal nerve modulation.

FIG. 2 illustrates the role of renal nerve activity in the progression of chronic cardiac and renal diseases. Increased renal afferent (from the kidney to the brain) nerve activity 201 results in the increased systemic sympathetic tone 202 and vasoconstriction (narrowing) 203 of blood vessels. Increased resistance of blood vessels results in hypertension 204. Hypertension is a major contributor to the progression of chronic heart failure and renal failure as well as the acute events such as strokes and myocardial infarcts. Increased renal efferent (from the brain to the kidney) nerve activity 205 results in further increased afferent renal nerve activity, secretion of the renal hormone renin 206, and reduction of renal blood flow and the decreased water and sodium excretion by the kidney. Renin contributes to systemic vasoconstriction of blood vessels 203. In combination these renal factors result in fluid retention 207 and increased workload of the heart thus contributing to the further deterioration of the patient. It should be clear from the FIG. 2 that moderation of renal nerve activity will benefit patients with heart, kidney and circulatory system (cardiorenal) diseases.

Figure 3:
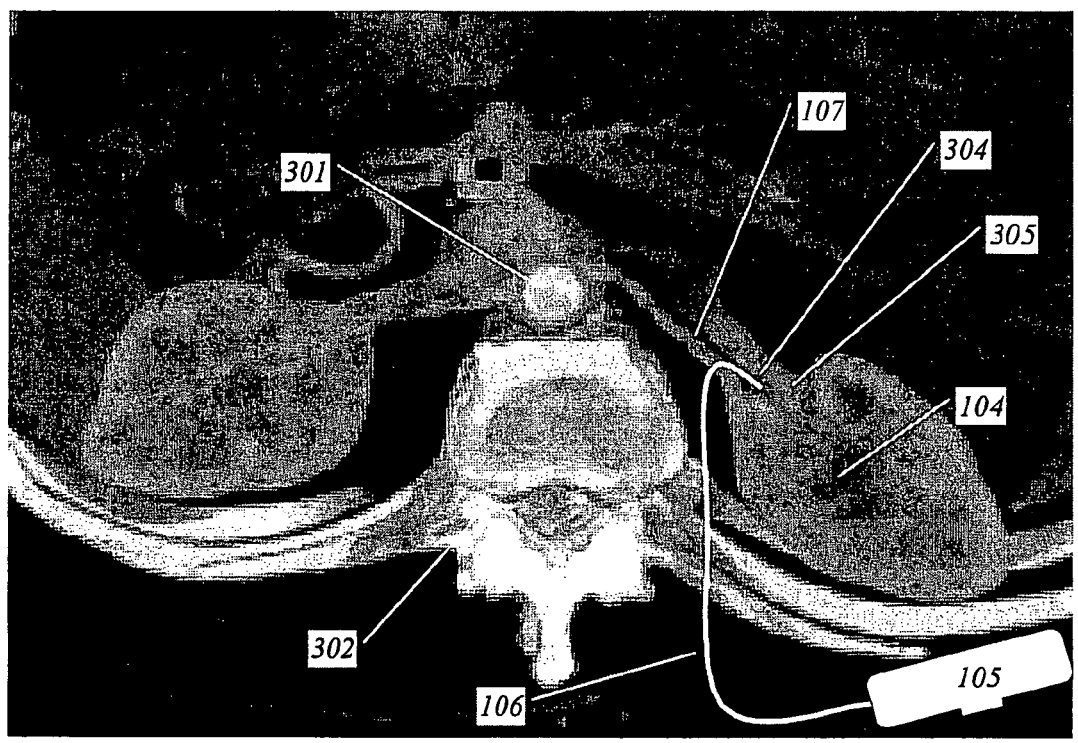
FIG. 3 illustrates anatomic positioning of the renal nerve blocking device.

FIG. 3 illustrates a preferred embodiment of the invention using a CT scan (digital X-ray) image of a human body. The pump 105 is implanted under the skin in the patient's back. The pump is equipped with the catheter 106. Tip 304 of the catheter resides near the renal artery 107. In this example, the tip 304 is shown in the hilum 305 area of the kidney where the renal blood vessels (arteries and veins) enter and exit the kidney. In clinical practice, the tip could reside in other locations within the renal periarterial space as long as the position allows the spread of the nerve blocking agent to at least a sufficient area of the nerve to achieve the required level of nerve blockade. Each kidney has an outer convex surface and an indentation on the inner side called the hilum. The hilum functions as a route of entry and exit for the blood vessels, lymph vessels, nerves and ureters of the kidney. Renal nerves follow the renal artery 107 that connects the kidney 104 to the aorta 301 shown in front of the spine 302. Kidney and renal vessels are enclosed in fat and fascia made of connective tissues that do not show well on this type of CT scan image.

It is significant that the catheter 106 can be introduced into the periarterial space under the CT guidance without surgery. The spatial resolution of modern imaging modalities such as CT, CT Fluoroscopy, Ultrasound and MRI allows an interventional radiologist to position the catheter within a millimeter from the renal artery of a human. The procedure is performed using a needle, an exchange guidewire and similar techniques commonly used in interventional radiology. The distal end of the catheter can be left outside of the body for the test period or the entire treatment if the treatment requires only a short duration. Later, if the renal nerve blocking therapy is clinically successful, an implanted pump or a simple subcutaneous port such as a commercially available Port-A-Cath device can be connected to the already implanted catheter for repeat infusions of the nerve-blocking drug.

Figure 4:
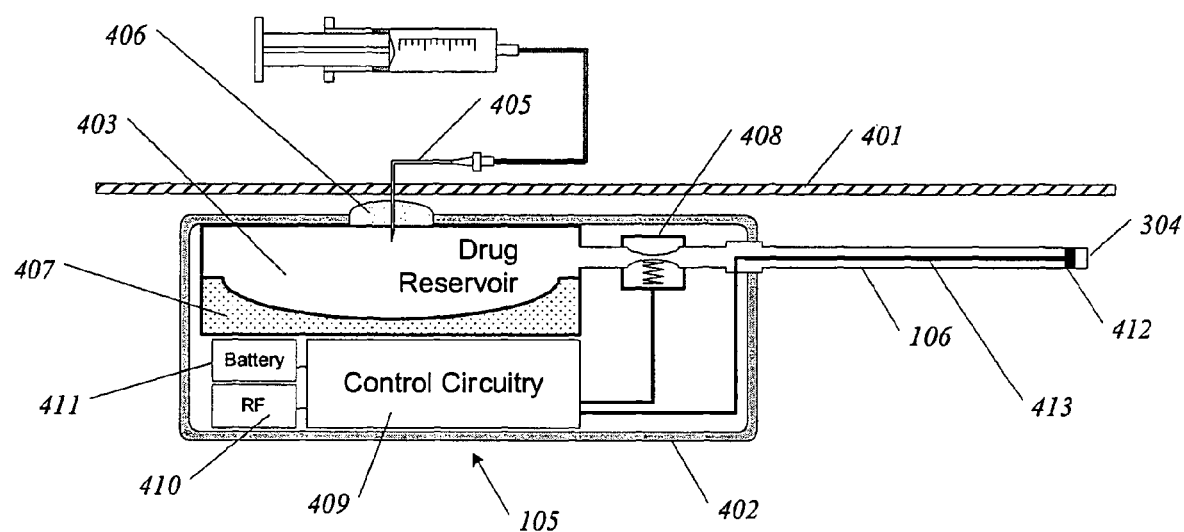
FIG. 4 illustrates an implantable drug infusion pump with a catheter electrode.

FIG. 4 illustrates a simplified design of an implantable programmable drug infusion pump. The pump 105 in implanted in a pocket under the patient's skin 401. All the mechanisms of the pump are enclosed in a titanium or polymer case 402. Drug is stored in the reservoir 403. To refill the pump a needle 405 is used to puncture the skin and the pump reservoir septum 406. Septum 406 is made of a material such as silicon that seals after the puncture. Drug is displaced from the reservoir by the compressed propellant 407. The propellant can be a chlorofluorocarbon, butane or other similar compound. The propellant acts on the drug through the elastic diaphragm 408. Alternatively, the diaphragm can act as a spring or it can be acted upon by the spring to displace the drug. The catheter 106 is in fluid communication with the reservoir 403. The propellant urges the drug from the reservoir into the catheter and through the catheter to the site of delivery, in this case, periarterial space of the renal artery and the renal nerve. To control the release of the drug, a valve 408 is placed between the reservoir and the catheter. The valve is normally closed. When it is forced open by the pump electronic control circuitry 409 for a short duration of time, a bolus of drug is released from the pump to the renal nerve-blocking site. The internal battery 411 supplies energy to the electronics and the valve. The communication electronics 410 allows the physician to reprogram the pump altering the amount and frequency of drug delivery as well as to interrogate the device. The communication electronics can be a radio-frequency RF link. All the elements described above are known to the developers of implantable drug pumps.

Programmable implantable infusion devices (also called implantable pumps) that actively meter the drug into an associated drug delivery catheter are described in the U.S. Pat. Nos. 4,692,147; 5,713,847; 5,711,326; 5,458,631; 4,360,019; 4,487,603; and 4,715,852. Alternatively, implantable infusion devices can control drug delivery by means of a rate-limiting element positioned between the drug reservoir and the delivery catheter as described in the U.S. Pat. No. 5,836,935, or by only releasing drug from the reservoir upon application of pressure to a subcutaneously positioned control device as described in U.S. Pat. Nos. 4,816,016 and 4,405,305. Implantable infusion devices have been used for intravenous, intraarterial, intrathecal, intraperitoneal, intraspinal and epidural drug delivery but not for periarterial drug infusion.

Known infusion pumps described above can be used to block the renal nerve for the purpose of treating cardiac diseases but they lack certain features needed in practical application. It is important for the physician to be able to determine that the nerve is in fact effectively blocked. In pain control applications of local anesthetics, the disappearance of the pain by itself is an indicator of an effective block. There is no natural indication of the renal nerve activity that can be simply measured. To address that problem, the pump 105 is equipped with a test electrode 412 on the tip 304 of the catheter 106. The electrode can be a single ring or multiple electrodes made of a conductive metal such as gold, stainless steel or titanium. The electrode 412 is connected to the control circuitry of the pump 409 by a conductive wire 413 integrated inside the catheter body 106. Except for the tip electrode 412 the wire is electrically insulated from the patient.

To test the effectiveness of the renal nerve block the control circuitry initiates an electric pulse to the electrode. To close the electric circuit the metal case 402 of the pump can be used as a second return electrode. Alternatively the catheter 106 can be equipped with more than one electrode. Low electric current pulse that can be in the range of 5-10 milliamps is passed through the tissue surrounding the electrode 412. If the nerve block is effective, patient will have no sensation of tingling or minor electric shock. If the block is ineffective, the nerves in the surrounding tissue will conduct the pulse, causing pain that the patient then reports to the physician and the physician will be able to make adjustments to therapy such as, for example, increase the dose of drug delivered by the pump.

This aspect is similar to the surgical technique used by anesthesiologists to establish short term invasive nerve blocks during surgery. Before the start of the surgery, the anesthesiologist places a needle precisely on the nerve or plexus. To do this, a specially designed electrical nerve stimulator is used. The nerve stimulator delivers a very small electrical current, too small to be felt, to the nerve, which causes twitching of the particular muscles supplied by that nerve or plexus of nerves. In this example, the nerve serves as nothing more than a sophisticated "electrical wire", which is now conducting the current delivered by an electrical device to the muscles, in place of the normally conducted current originating from the brain. The patient will therefore experience small muscle twitches in the muscles supplied by that nerve similar to when your eye is twitching. This technique has never been previously applied to an implanted device. In the proposed invention, the physician will be able to perform the nerve block test in their office, without sophisticated surgical techniques and sterile environment. The external programmer device will initiate a command sequence that will be received by the electronics of the implanted pump using RF waves.

In an alternate embodiment, the catheter can have two or more sets of electrodes, at least one set proximal to and at least one set distal to the area of renal nerve blockade. Each set of electrodes is in sufficient proximity to the renal nerve so that it can either sense intrinsic nerve activity or stimulate nerve activity. It is clear that if the pump control circuitry initiates and electrical pulse to a one set of electrodes on one side of the block and does not record a corresponding and appropriately timed signal on the opposite side of the block, then the drug is effective in creating the nerve block. Conversely, if the electrical activity is sensed, more drug must be infused to create the desired block. It is also clear that this information can be used as feedback by the control circuitry to automatically adjust the timing and/or amount of drug released.

Figure 5:
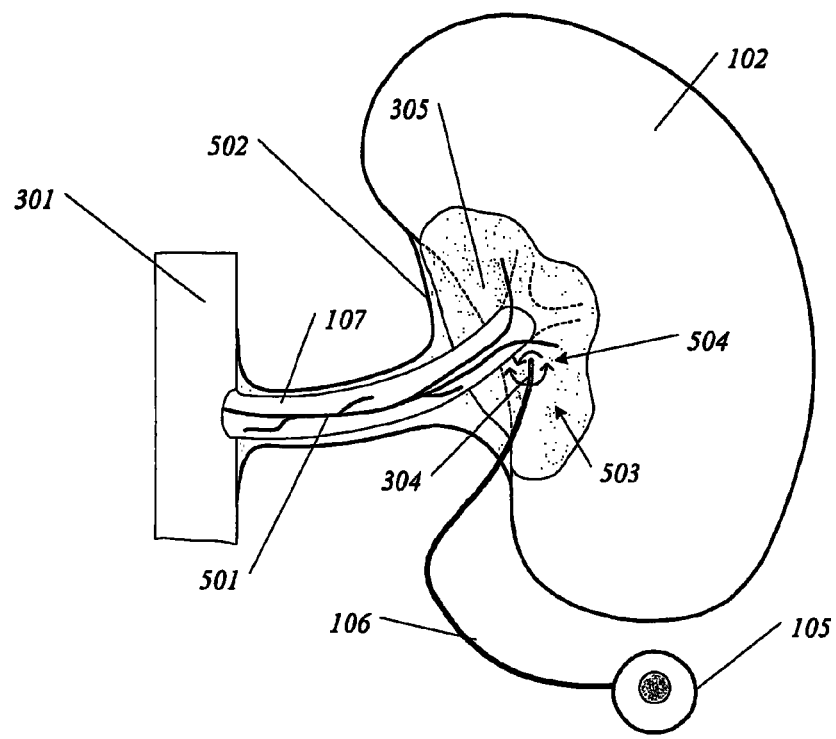
FIG. 5 illustrates the infusion of an anesthetic drug into the renal fatpad.

FIG. 5 illustrates the anatomic placement of the drug infusion catheter 106 in the periarterial space of the renal artery. Catheter 106 is shown schematically in connection to the implanted pump 105. The kidney 102 is supplied with blood by the renal artery 107 from the aorta 301. The periarterial space is defined as space immediately surrounding the renal arteries and veins along its length between the connection to the aorta and the hilum 305 of the kidney. The renal artery can branch into two or more arteries. The renal vein and its branches connecting the kidney to the vena cava of the patient share the space. These additional elements of the renal vascular system are omitted on FIG. 5 and the following figures for clarity but are presumed there.

Renal nerve 501 is shown schematically as a branching network attached to the external surface of the renal artery 107. Anatomically, the renal nerve forms one or more plexi on the external surface of the renal artery. Fibers contributing to these plexi arise from the celiac ganglion, the lowest splanchnic nerve, the aorticorenal ganglion and aortic plexus. The plexi are distributed with branches of the renal artery to vessels of the kidney, the glomeruli and tubules. The nerves from these sources, fifteen or twenty in number, have a few ganglia developed upon them. They accompany the branches of the renal artery into the kidney; some filaments are distributed to the spermatic plexus and, on the right side, to the inferior vena cava.

A fibrous connective tissue layer, called the renal capsule, encloses each kidney. Around the renal capsule is a dense deposit of adipose tissue, the renal fat pad, which protects the kidney from mechanical shock. The kidneys and the surrounding adipose tissue are anchored to the abdominal wall by a thin layer of connective tissue, the renal fascia. The periarterial space of the renal artery is externally limited by renal fascia 502 that extends between the kidney and the aorta and contains renal vessels and nerves. Renal fascia presents a natural barrier to the dissipation of the infused drug 504 that is emitted from the tip of the catheter 106. Fat fills the space between the fascia and the renal artery. In particular, there is a fat tissue layer 503 in the hilum of the kidney that surrounds the renal pedicle where arteries, nerves and veins enter the kidney. The catheter tip 304 is shown penetrating the renal fascia and the renal fat and the anesthetic drug is infused into the fatpad tissue. Although shown in the hilum of the kidney, the tip can be placed anywhere in the renal periarterial space as long as the position allows the spread of the nerve blocking agent to at least a sufficient area of nerve to achieve the required level of nerve blockade. In practice, there is an advantage to placing the tip at a location in continuity with the periarterial space fat. Anesthetic drugs such as amino ester and amino amide local anesthetics such as bupivacaine have high lipid solubility. The invention takes advantage of this. A single bolus of bupivacaine, after being infused into these areas, will be adsorbed by fat and retained at the location of the renal nerve. In this manner, the renal fat serves as storage of drug that will then be slowly released from the renal fat, and in this way, obtains the desired prolonged nerve blocking action.

Figure 6:
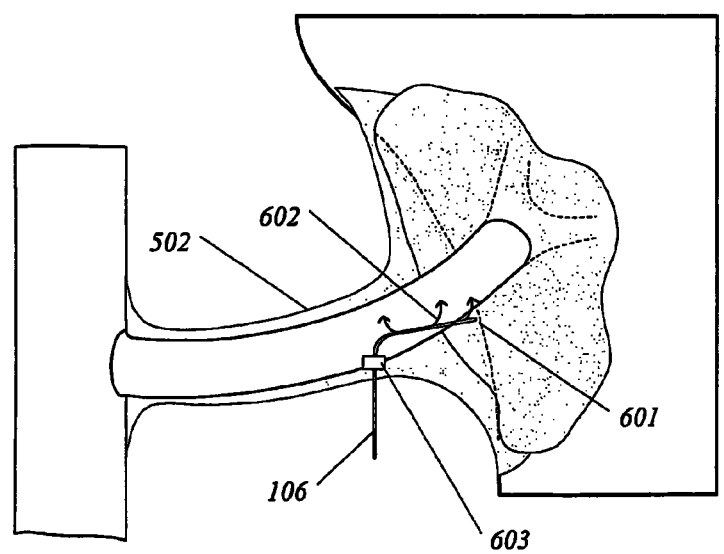
FIG. 6 illustrates a catheter with a cuff for distributed drug infusion into the periarterial space.

FIG. 6 illustrates an alternative embodiment of the invention where the catheter 106 has a sealed tip 601 but is equipped with multiple side holes or pores 602 in the wall of the catheter. The pores can be as small as a micron in diameter. Pores less than 20 microns in diameter will allow penetration of the nerve-blocking drug through the wall of the catheter and into the periarterial space, renal fat pad and ultimately to the renal nerve target. At the same time, these small pores will discourage ingrowth of tissue into the side holes and increase the probability of the catheter patency after being implanted in the body for a long time. This design helps redistribute the anesthetic in the periarterial space between the wall of the renal artery and the renal fascia 502. The catheter is equipped with a cuff 603 to encourage ingrowth of connective tissue and prevents escape of the infused drug through the puncture in the renal fascia. The cuff can be made of a natural or synthetic fiber material with pores larger than 20 microns and preferably 100 microns. For example, Dacron cuffs are commonly used in surgically implanted catheters for long term vascular access and dialysis in humans, Dacron cuffs support ingrowth of tissue, prevent dislodgment and provide a barrier to infection.

Figure 7:
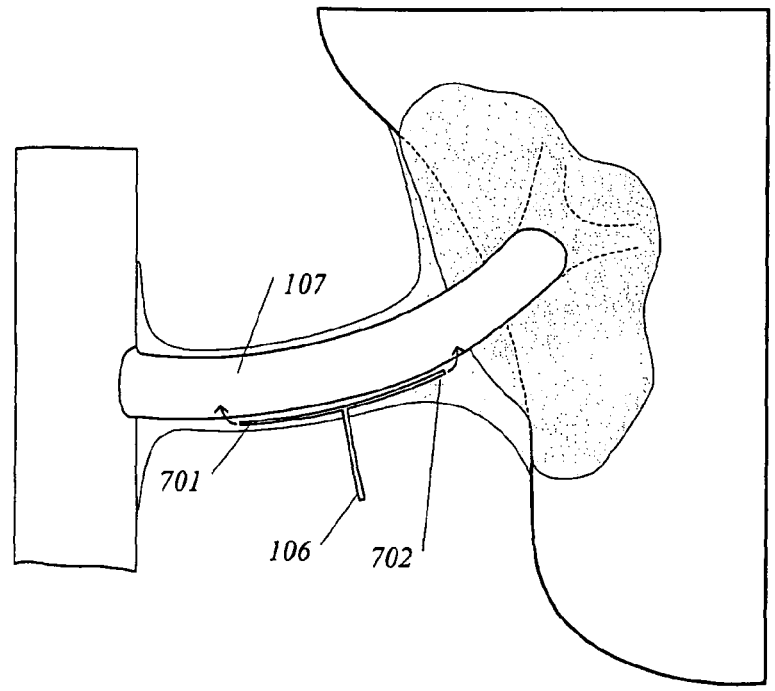
FIG. 7 illustrates a bifurcated catheter for drug infusion into the periarterial space.

FIG. 7 illustrates an embodiment of the catheter 106 that bifurcates in the periarterial space of the kidney after it enters inside the renal fascia. The internal lumen of the catheter is split between two or more branches 701 and 702. Catheter brunches can have end holes; side holes or wall pores for the delivery of medication to the renal nerve.

Figure 8:
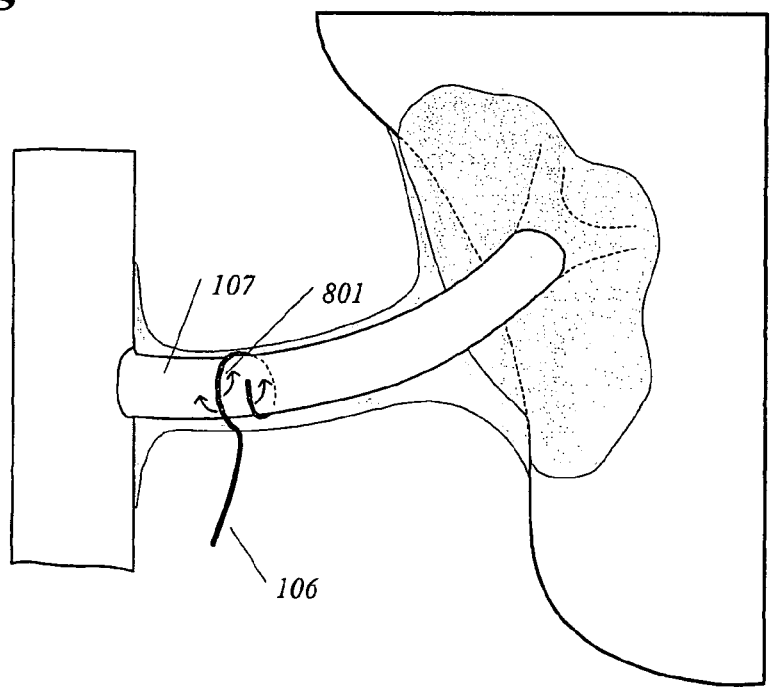
FIG. 8 illustrates a coiled catheter for drug infusion into the periarterial space.

FIG. 8 illustrates an embodiment of the catheter 106 that forms a coil 801 inside the periarterial space. The coil can be equipped with side holes or pores to evenly distribute the infused drug in the periarterial space around the renal artery.

Figure 9:
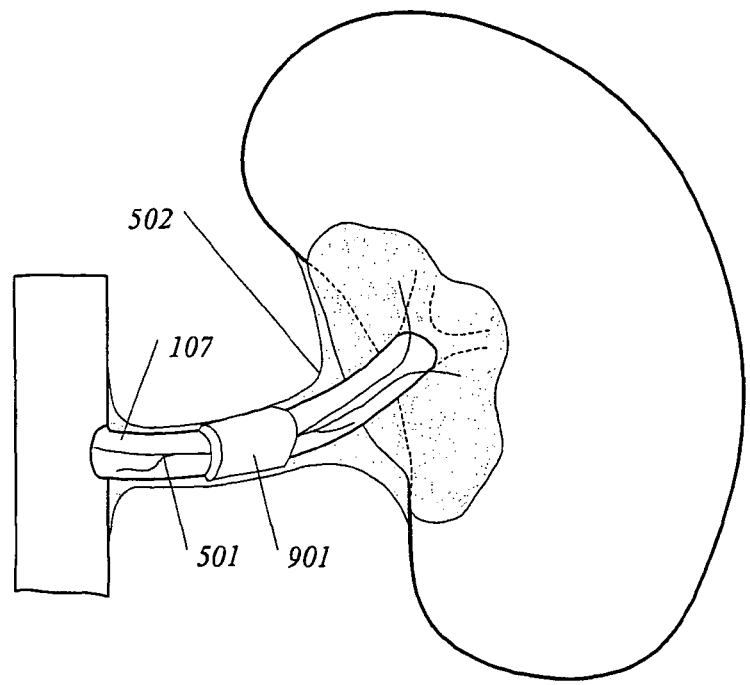
FIG. 9 illustrates a drug eluting implant in the periarterial space.

FIG. 9 illustrates an alternative preferred embodiment of the invention. The nerve blocking agent is stored in the drug eluting implant 901. The implant 901 is contained in the periarterial space after the implantation surgery. Implant can be permanent or slowly biodegradable. Prior to implantation the implant is impregnated or "loaded" with a nerve-blocking agent that is gradually released over time into the periarterial space in the amount sufficient to block the renal nerve. An implantable drug eluting implant or pellet(s) made of a non-biodegradable polymer has the drawback of requiring both surgical implantation and removal. Use of a biocompatible, biodegradable implant overcomes deficiencies of nonbiodegradable implants. A biodegradable implant can release a drug over a long period of time with simultaneous or subsequent degradation of the polymer within the tissue into constituents, thereby avoiding any need to remove the implant. A degradable polymer can be a surface eroding polymer. A surface eroding polymer degrades only from its exterior surface, and drug release is therefore proportional to the polymer erosion rate. A suitable such polymer can be a polyanhydride. It is advantageous to have a surface eroding implant where the eroding surface faces the renal artery and the renal nerve. Other surfaces of the implant may be designed to erode at a slower rate or not erode at all that directing the drug towards the renal nerve target.

Implants for long-term drug delivery are known. For example, such implants have been used or proposed for delivering a birth control drug systemically (into circulation) or a chemotherapeutic agent to a localized breast tumor. Examples of such implantable drug delivery devices include implantable diffusion systems (see, e.g., implants such as Norplant for birth control and Zoladex for the treatment of prostate cancer) and other such systems, described of example in U.S. Pat. Nos. 5,756,115; 5,429,634; 5,843,069. Norplant is an example of a class of the drug eluting implants also called controlled release systems comprising a polymer for prolonged delivery of a therapeutic drug. Norplant is a subdermal reservoir implant comprised of a polymer can be used to release a contraceptive steroid, such as progestin, in amounts of 25-30 mg/day for up to sixty months. Norplant uses the DURIN biodegradable implant technology that is a platform for controlled delivery of drugs for periods of weeks to six months or more. DURIN can be adopted for delivery of an anesthetic into the periarterial space. The technology is based on the use of biodegradable polyester excipients, which have a proven record of safety and effectiveness in approved drug delivery and medical device products. DURIN technology is available from the DURECT Corporation of Cupertino, Calif.

Drug eluting implants generally operate by simple diffusion, e.g., the active agent diffuses through a polymeric material at a rate that is controlled by the characteristics of the active agent formulation and the polymeric material. An alternative approach involves the use of biodegradable implants, which facilitate drug delivery through degradation or erosion of the implant material that contains the drug (see, e.g., U.S. Pat. No. 5,626,862). Alternatively, the implant may be based upon an osmotically-driven device to accomplish controlled drug delivery (see, e.g., U.S. Pat. Nos. 3,987,790, 4,865,845, 5,057,318, 5,059,423, 5,112,614, 5,137,727, 5,234,692; 5,234,693; and 5,728,396). These osmotic pumps generally operate by imbibing fluid from the outside environment and releasing corresponding amounts of the therapeutic agent. Osmotic pumps suitable for the renal nerve blocking application are available from ALZA Corporation of Mountain View, Calif. under the brand name of Alzet Osmotic Pumps and the Duros implant. Duos implant is a miniature cylinder made from a titanium alloy, which protects and stabilizes the drug inside. Water enters into one end of the cylinder through a semipermeable membrane; the drug is delivered from a port at the other end of the cylinder at a controlled rate appropriate to the specific therapeutic agent. The advantage of drug eluting implants is that they can store a common anesthetic agent in concentration much higher than that used for common local anesthetic injections. Accurate delivery of small amounts of the drug via diffusion enables storage of the many months supply of the nerve-blocking agent in the implant and eliminates the need for frequent refills typical of an implanted drug pump. It is also clear that more than one drug can be released from the implant, that function in either in a complementary or inhibiting manner, to enhance or block the activity of each other.

Figure 9A:
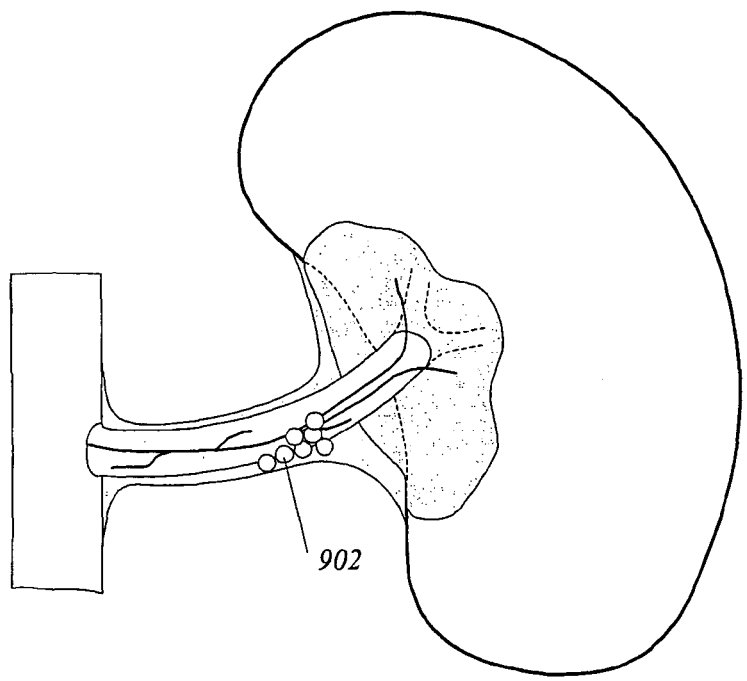
FIG. 9A illustrates a drug eluting biodegradable material in the periarterial space.

FIG. 9A illustrates an alternative embodiment of the local drug eluting system illustrated by FIG. 9. In this embodiment the sustained release of the nerve-blocking agent is accomplished by infusing or implanting a self-forming biodegradable compound impregnated with the nerve-blocking agent in the periarterial space around the renal artery. The nerve-blocking agent is delivered in a biodegradable matrix such as an injectable get or microspheres. The action of the nerve-blocking drug is thus prolonged and can be enhanced by adding other medicaments, such as steroids, that suppress inflammation at the application site. This embodiment has an advantage of allowing better distribution and conformance of the drug eluting implant to the anatomic space surrounding the renal nerve. The carrier matrix loaded with the nerve blocking drug can be applied as a patch by the surgeon to the surface of the renal artery. Then the periarterial space will be closed and the fascia repaired. Alternatively the carrier matrix can be delivered through a needle attached to an infusion device. Such needle can be inserted into the periarterial space under CT guidance as illustrated by FIG. 3. For delivery through a needle the matrix will need to be in the form of gel or injectable microspheres.

Patches and gels containing local anesthetics have been previously used for topical application to numb skin at the site of irritation or burn as well as for example during cataract eye surgery. One applicable gel is described in the U.S. Pat. No. 5,589,192 to Okabe, et al. "Gel pharmaceutical formulation for local anesthesia."

Injectable microparticles or microspheres or microcapsules loaded with drugs are also known. Injectable microspheres are made of degradable materials, such as lactic acid-glycolic acid copolymers, polycaprolactones and cholesterol among others. For example, U.S. Pat. No. 5,061,492 related to prolonged release microcapsules of a water-soluble drug in a biodegradable polymer matrix which is composed of a copolymer of glycolic acid and a lactic acid. The injectable preparation is made by preparing a water-in-oil emulsion of aqueous layer of drug and drug retaining substance and an oil layer of the polymer, thickening and then water-drying. In addition, controlled release microparticles containing glucocorticoid (steroid) agents are described, for example, by Tice et al. in U.S. Pat. No. 4,530,840. In another embodiment, the implanted microspheres are stable and do not degrade on their own. In this case, the microspheres are broken via external, directed application of an energy source, such as ultrasound, temperature or radiation. Breaking of the microspheres release the encapsulated drug and provide the desired physiologic effect, in this case, nerve blockade.

U.S. Pat. No. 5,700,485 to Berde, et al. titled "Prolonged nerve blockade by the combination of local anesthetic and glucocorticoid" describes in sufficient detail methods of manufacturing and application of biodegradable controlled release microspheres for the prolonged administration of a local anesthetic agent. The microspheres are formed of biodegradable polymers polyanhydrides, polylactic acid-glycolic acid copolymers. Local anesthetics are incorporated into the polymer. Prolonged release is obtained by incorporation of a glucocorticoid into the polymeric matrix or by co-administration of the glucocorticoid with the microspheres. Significantly U.S. Pat. No. 6,238,702 to the same authors entitled "High load formulations and methods for providing prolonged local anesthesia" described the polymer matrix that contained significantly higher concentration of local anesthetic than is normally used for injections. Since the periarterial space can anatomically accommodate an implant of substantial size nerve blocking for at least 30 days and more preferably several years is possible. U.S. Pat. No. 5,618,563 to Berde, et al. titled "Biodegradable polymer matrices for sustained delivery of local anesthetic agents" further elaborates on the biodegradable controlled release system consisting of a polymeric matrix incorporating a local anesthetic for the prolonged administration of the local anesthetic agent, and a method for the manufacture thereof.

Figure 10:
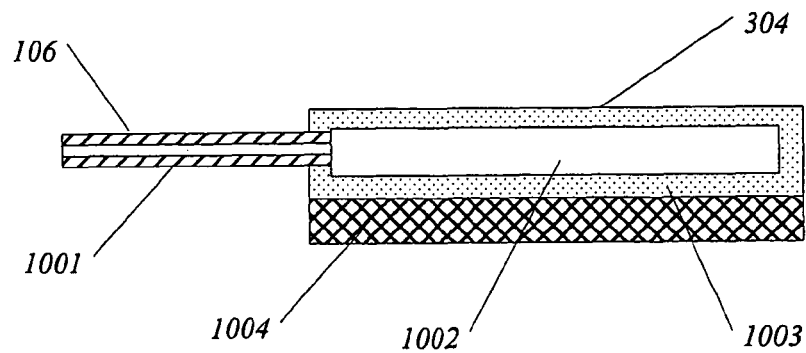
FIG. 10 illustrates a porous drug infusion catheter.

FIG. 10 illustrates the design of the drug delivery catheter for the invention that improves fixation of the catheter and distribution of the infused drug in the periarterial space. After the implantation an implant and the surrounding tissue undergo changes. It is the purpose of this part of the invention to improve the interface of the drug delivery device to maximize the effect of the drug on the nerve while minimizing the amount.

The human body acts spontaneously to reject or encapsulate any foreign object, which has been introduced into the body or a specific bodily organ. In some cases, encapsulation will impede or halt drug infusion. In others, the delivery fluid will reflux from the tissue through a space opened between the exterior of the catheter and the tissue of the bore in which the catheter is received. Either of these results will greatly diminish the effect of direct infusion of medicaments on affected body tissue. Thus, the body's own natural defense systems thus tend to frustrate the procedure. The reaction of living tissue to an implant can take a number of different forms. For example, the initial response to the surgical trauma of implantation is usually called the acute inflammatory reaction and is characterized by an invasion of polymorphonuclear leukocytes (PMNs). The acute inflammatory reaction is followed by the chronic inflammatory reaction, which is characterized by the presence of numerous macrophages and lymphocytes, some monocytes and granulocytes. Fibroblasts also begin accumulating in the vicinity of the implant and begin producing a matrix of collagen. The fibroblasts and collagen form a connective tissue capsule around the implant and the chronic inflammatory cells to effectively isolate the implant and these cells from the rest of the body. Connective tissue consisting of a fine network of collagen with active producing fibroblasts accompanied by chronic inflammatory cells, capillaries and blood vessels is referred to collectively as granulation tissue.

Thus, when a material is implanted into a soft tissue bed of a living organism such as a human or an animal, a granulation tissue capsule is formed around the implant material consisting of inflammatory cells, immature fibroblasts and blood vessels. This tissue capsule usually increases in thickness with time and contracts around the implant, deforming the implantation site, and possibly the implant itself depending upon the rigidity of the implant.

Implant illustrated by FIG. 10 is the tip 304 of the drug delivery catheter 106 connected to the implanted drug pump explained earlier in this application. The tip 304 is in the fluid communication with the internal lumen 1001 of the catheter and is shown with an internal cavity 1002 to which the nerve-blocking drug is delivered by the pump 104 (See FIG. 4). The tip is made out of the porous material, preferably a porous plastic such as for example PTFE. It is known that, when the implant is porous with pore entry diameters larger than approximately 20 microns, tissue grows into these pores. This phenomenon appears desirable to many medical device application because it makes an implant one with the implanted organ and in theory it allows tissue ingrowth into the implant and reduces capsular contraction. For example, U.S. Pat. No. 4,011,861 to Enger discloses an implantable electric terminal which has pores preferably in the range of about 10 to 500 microns so that blood vessels and tissue can grow into the pores.

The embodiment illustrated by FIG. 10 combines a material with small pores, preferably less than 20 microns 304 designed to discourage the tissue ingrowth and a material with larger pores, preferably larger than 20 microns 1004 to encourage tissue ingrowth. Material 1003 allows free diffusion and convection of the drug from the cavity 1002 to the periarterial space. Material 1004 encourages the natural fixation of the catheter tip 304 so that it will not be dislodged by motion and migrate out of the periarterial space.

Figure 11:
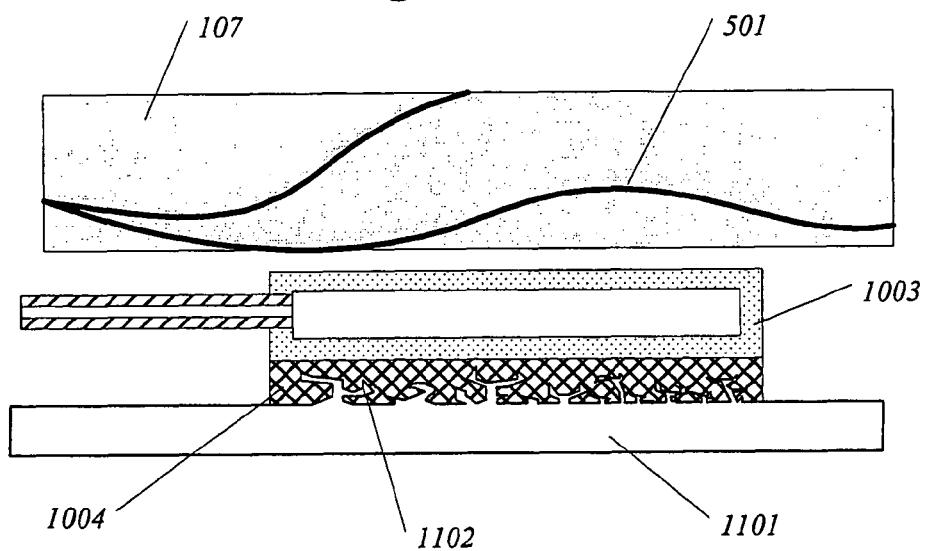
FIG. 11 illustrates a drug infusion catheter with tissue ingrowth.

FIG. 11 illustrates the catheter tip made of porous materials. It shows the surrounding tissue 1101 ingrowth 1102 into the large pore implant 1004 section. The small pore section 1003 is oriented to direct the drug infusion towards the renal artery 107 and the renal nerve 501.

Figure 12:
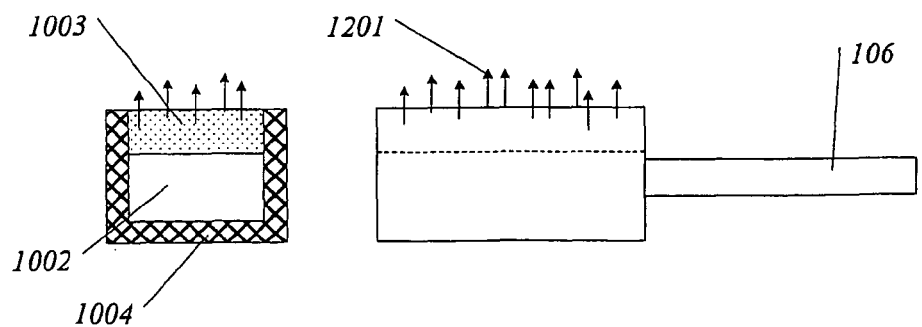
FIG. 12 illustrates the drug infusion catheter that directs the drug towards the renal nerve.

FIG. 12 further illustrates an embodiment of the porous tip of the catheter 106 for directional drug delivery. The portion of the implant that surrounds the drug filled cavity 1002 and that is oriented away from the renal nerve is made of the material 1004 that is impermeable to drug. Portion of the implant that is oriented towards the renal nerve (on the surface of the renal artery) 1003 is made of the material that is permeable to the nerve blocking agent. Drug flux 1201 is shown as unidirectional therefore directing the therapy towards the site and minimizing the loss of the drug.

FIGS. 13 and 14 further illustrate an embodiment of the porous tip of the catheter 106 that at least partially encloses or envelopes the renal artery 107 with the intention of further directing the drug delivery towards the renal nerve. The tip forms a multi-layer cuff around the artery. The outer shell 1004 of the cuff is made of the material that is impermeable to the infused drug to prevent dissipation of the said drug away from the renal nerve. The material 1004 can also have large pores to encourage ingrowth and fixation of the implant. The inner layer 1003 is made of material permeable to the nerve-blocking drug. It is in fluid communication with the delivery catheter 106. The layer 1003 can be equipped with internal channels to facilitate equal distribution of drug 1201 in the space 1301 between the cuff and the artery 107.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of treating a patient diagnosed with at least one of heart failure, hypertension, acute myocardial infarction, renal disease, or chronic renal failure, the method comprising:
   delivering a neuromodulatory agent to a nerve that innervates a kidney of the patient; and
   at least partially blocking neural activity along the nerve with the neuromodulatory agent and modulating at least one of urine production, blood pressure, fluid retention, renin secretion, renal blood flow, waste excretion, and sodium retention in the patient,
   wherein delivering a neuromodulatory agent to a nerve that innervates a kidney of the patient comprises delivering the neuromodulatory agent via an intravascular to extravascular approach.

2. The method of claim 1 wherein delivering a neuromodulatory agent to a nerve that innervates a kidney of the patient comprises delivering at least one of an anesthetic, neurotoxin, alcohol, phenol, ketamine, and antidepressant to the nerve.

3. The method of claim 1 wherein delivering a neuromodulatory agent to a nerve that innervates a kidney of the patient comprises delivering a neuromodulatory agent via a catheter.

4. The method of claim 3 wherein a distal portion of the catheter comprises at least two electrodes, and wherein the method further comprises sensing neural activity via the electrodes.

5. The method of claim 3 wherein a distal portion of the catheter comprises at least two electrodes, and wherein the method further comprises electrically stimulating a renal nerve of the patient via the electrodes.

6. The method of claim 5 wherein the distal portion of the catheter comprises a first electrode configured to be located proximally of a nerve modulating site and a second electrode configured to be located distally of the nerve modulating site, and wherein the method further comprises sensing neural activity via the first and second electrodes.

7. The method of claim 5 wherein the distal portion of the catheter comprises a first electrode configured to be located proximally of a nerve modulating site and a second electrode configured to be located distally of the nerve modulating site, and wherein the method further comprises electrically stimulating a renal nerve of the patient with the electrodes.

8. The method of claim 1, further comprising determining whether neural activity has been sufficiently altered.

9. The method of claim 1 wherein at least partially blocking the neural activity comprises at least substantially blocking sympathetic neural activity along a renal nerve of the patient.

10. The method of claim 9, further comprising determining whether neural activity along the renal nerve has been substantially blocked.

11. The method of claim 10 wherein determining whether neural activity has been substantially blocked comprises electrically stimulating the renal nerve and detecting a response in the patient.

12. The method of claim 1 wherein delivering a neuromodulatory agent to a nerve that innervates a kidney of the patient comprises delivering a neuromodulatory agent via a drug delivery device.

13. The method of claim 1 wherein delivering a neuromodulatory agent to a nerve that innervates a kidney of the patient comprises positioning a needle within a periarterial space of the patient and injecting the neuromodulatory agent via the needle into the periarterial space of the patient.

14. The method of claim 13 wherein positioning a needle proximate the periarterial space of the patient comprises positioning the needle under CT guidance.

* * * * *